United States Patent [19]

Morozowich

[11] 4,100,192

[45] Jul. 11, 1978

[54] INTER-PHENYLENE-PG AMIDES

[75] Inventor: Walter Morozowich, Kalamazoo Township, Kalamazoo County, Mich.

[73] Assignee: The Upjohn Company, Kalamazoo, Mich.

[21] Appl. No.: 788,455

[22] Filed: Apr. 18, 1977

[51] Int. Cl.² .................................................. C07C 103/20
[52] U.S. Cl. .................................. 260/558 R; 544/173; 544/391; 544/174; 260/239 B; 260/295 H; 260/295 AM; 260/295 R; 260/293.76; 260/313.1; 260/290; 260/551 R; 260/556 CN; 260/557 R; 260/557 H; 260/558 H; 260/559 H; 260/559 R; 260/555 D; 260/465 D; 542/426; 542/429; 560/36
[58] Field of Search ............ 260/558 R, 558 D, 559 R

[56] References Cited

U.S. PATENT DOCUMENTS

| | | | |
|---|---|---|---|
| 3,933,895 | 1/1976 | Nelson | 260/473 A |
| 3,933,897 | 1/1976 | Nelson | 260/473 A |
| 3,933,898 | 1/1976 | Nelson | 260/473 A |
| 3,933,899 | 1/1976 | Nelson | 260/473 A |
| 3,933,900 | 1/1976 | Nelson | 260/473 A |
| 4,054,604 | 10/1977 | Bernady et al. | 260/559 H |

*Primary Examiner*—Arthur P. Demers
*Attorney, Agent, or Firm*—Robert A. Armitage

[57] ABSTRACT

The present invention relates to novel amido, cycloamido, carbonylamido, sulfonylamido, and hydrazino derivatives of inter-phenylene-PG-type compounds. These novel derivatives produce surprisingly prolonged oral activity, particularly as anti-thrombotic agents, as compared to the previously known inter-phenylene-PG-type acids and esters.

46 Claims, No Drawings

INTER-PHENYLENE-PG AMIDES

BACKGROUND OF THE INVENTION

The present invention relates to novel amido, cycloamido, carbonylamido, sulfonylamido and hydrazino derivatives of inter-phenylene-PG-type compounds. Certain of these inter-phenylene-PG-type compounds are known in the art in free acid and ester form to be structural and pharmacological analogs of the prostaglandins.

The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions.

Likewise, the known inter-phenylene-PG-type compounds represent pharmacological agents exhibiting improved utility as compared to the known prostaglandins. Most especially, these known inter-phenylene-PG-type compounds are employed in the treatment and prevention of diseases whose etiology relates to abnormal or undesirable platelet aggregation.

The preparation of the known inter-phenylene-PG-type compounds is described in the art by a variety of chemical methods. For example, U.S. Pat. No. 3,933,898, issued Jan. 20, 1976, describes the preparation of a wide variety of inter-phenylene-inter-oxa-PG-type compounds. Particularly, there are described therein the preparation of inter-phenylene-oxa-PG compounds exhibiting PGFα-, PGFβ-, PGE-, PGA-, and PGB-type cyclopentane ring structures. Further, inter-phenylene-PG-type compounds corresponding to the inter-phenylene-oxa-type compounds described above are described and prepared in German Offenlegungsschrift No. 2,635,838.

Moreover, in addition to the various inter-phenylene- and inter-phenylene-oxa-PG type compounds of the various cyclopentane ring structures referred to above, there are prepared in United States Ser. No. 614,242, filed Sept. 17, 1975 various inter-m-phenylene- and inter-m-phenylene-3-oxa-PG-type compounds exhibiting the following cyclopentane ring structures: PGD, 9-deoxy-PGD, and 9,10-didehydro-9-deoxy-PGD.

Finally, inter-phenylene-PG-type compounds exhibiting 11-deoxy-PGE, 11-deoxy-PGFα or 11-deoxy-PGFβ ring type structures are prepared from the above compounds by known methods for prostaglandin cyclopentane ring transformation. See, for example, Netherlands published application No. 7,309,856, abstracted at Derwent Farmdoc CPI No. 10695B, wherein the transformation of PGA-type compounds to corresponding 11-deoxy-PG-type compounds is described. Moreover, see Belgian Pat. No. 820,008, abstracted at Derwent Farmdoc CPI No. 22475W, describing an independent synthesis of certain inter-phenylene- and inter-phenylene-oxa-11-deoxy-PG-type compounds.

In addition to the various procedures described above for the preparation of inter-phenylene-PG-type compounds, improved processes are now available for the synthesis of such compounds in free acid or ester form. See, for example, APPENDIX I, describing an improved process for the synthesis of these compounds.

In addition to the above art, which is descriptive of methods for preparing acids or ester derivatives of certain prostaglandin type compounds, the preparation of prostaglandin-type amides is likewise accomplished by known methods. For example, see U.S. Pat. No. 3,981,868, issued Sept. 21, 1976, for description of the preparation of certain amido and cycloamido derivatives of 11-deoxy-PG-type compounds.

Further, U.S. Pat. No. 3,954,741, issued May 4, 1976, describes the preparation of certain carbonylamide and sulfonylamido derivatives of various prostaglandin analogs.

Finally, French published application No. 2,235,929, abstracted at Derwent Farmdoc CPI No. 26297W, describes the preparation of certain PG-type hydrazino derivatives.

SUMMARY OF THE INVENTION

The present invention comprises the surprising and unexpected discovery that certain novel amido, cycloamido, carbonylamido, sulfonylamido, and hydrazino derivatives of inter-phenylene-PG-type compounds exhibit prolonged oral activity as pharmacological agents. Particularly, the present invention comprises the surprising and unexpected discovery that such nitrogen-containing derivatives (herein collectively referred to as "carboxyamides") of inter-phenylene-PG-type compounds are surprisingly and unexpectedly more useful than the corresponding known free acid and ester derivatives of such compounds as orally administered antithrombotic agents.

In particular, the present invention comprises: a prostaglandin analog of the formula

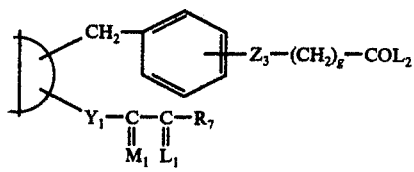

wherein D is

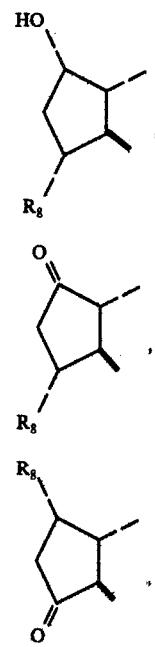

-continued

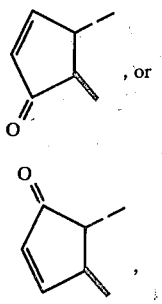, or

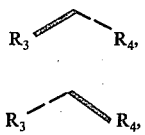, wherein
R$_8$ is hydrogen or hydroxy;
wherein Y$_1$ is
(1) trans-CH=CH—,
(2) cis-CH=CH—, or
(3) —CH$_2$CH$_2$—,
wherein g is one, 2, or 3;
wherein Z$_3$ is oxa or methylene,
wherein L$_1$ is

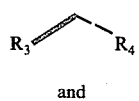

or a mixture of

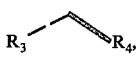

and

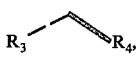

wherein R$_3$ and R$_4$ are hydrogen, methyl, or fluoro, being the same or different, with the proviso that one of R$_3$ and R$_4$ is methyl only when the other is hydrogen or methyl;
wherein M$_1$ is

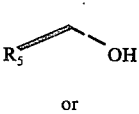

or

wherein
R$_5$ is hydrogen or methyl;
wherein R$_7$ is
(1) —(CH$_2$)$_m$—CH$_3$,

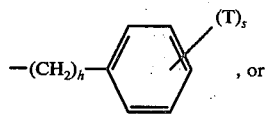, or

-continued

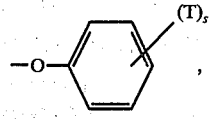, wherein h is zero to 3, inclusive, m is one to 5, inclusive, s is zero, one, 2, or 3, and T is chloro, fluoro, trifluoromethyl, alkyl of one to 3 carbon atoms, or alkoxy of one to 3 carbon atoms, the various T's being the same or different, with the proviso that not more than two T's are other than alkyl; and
wherein
L$_2$ is
(1) amino of the formula —NR$_{21}$R$_{22}$, wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive, hydroxyalkyl of one to 3 carbon atoms, inclusive, carboxy, alkoxycarbonyl of one to 4 carbon atoms, inclusive, or nitro; carboxyalkyl of one to four carbon atoms, inclusive; carbamoylalkyl of one to four carbon atoms, inclusive; cyanoalkyl of one to four carbon atoms, inclusive; acetylalkyl of one to four carbon atoms, inclusive; benzoylalkyl of one to four carbon atoms, inclusive, benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro; pyridyl; pyridyl substituted by one, 2, or 3 chloro, alkyl of one to 3 carbon atoms, inclusive, or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms, inclusive, hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of R$_{21}$ and R$_{22}$ is other than hydrogen or alkyl;
(2) cycloamino selected from the group consisting of

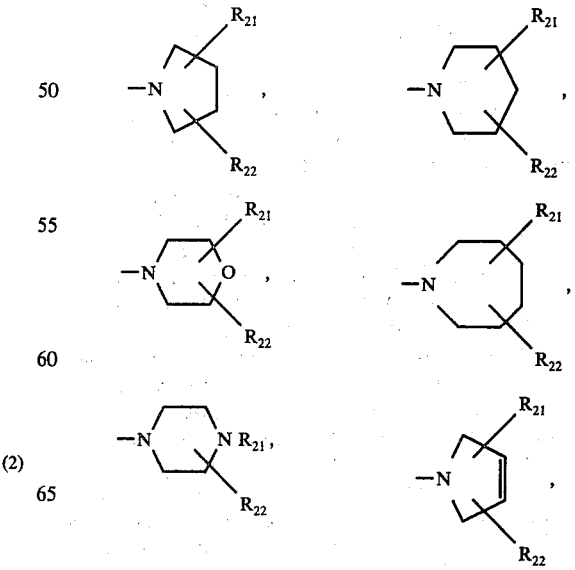

-continued or 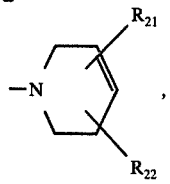

wherein $R_{21}$ and $R_{22}$ are as defined above;

(3) carbonylamino of the formula —$NR_{23}COR_{21}$, wherein $R_{23}$ is hydrogen or alkyl of one to 4 carbon atoms and $R_{21}$ is as defined above;

(4) sulphonylamino of the formula —$NR_{23}SO_2R_{21}$, wherein $R_{21}$ and $R_{23}$ are as defined above; or (5) hydrazino of the formula —$NR_{23}R_{24}$, wherein $R_{24}$ is amino of the formula —$NR_{21}R_{22}$, as defined above, or cycloamino, as defined above.

For convenience, the novel prostaglandin carboxyamides described above will be referred to by the trivial, art-recognized system of nomenclature described by N. A. Nelson, Journal of Medicinal Chemistry, 17, 911 (1974). Accordingly, 3,7-inter-m-phenylene-4,5,6-trinor-3-oxa-4,5,6-trinor-$PGE_1$, amide is represented by formula I, above, when $L_2$ is —$NH_2$, g is one, $Z_3$ is oxa and attached to the phenyl ring in the position meta to the attachment of the methylene, D is a PGE-type cyclopentane ring, $Y_1$ is trans—CH=CH—, $R_3$, $R_4$, and $R_5$ are all hydrogen and the hydroxy of the $M_1$ moiety is in the alpha configuration, and $R_7$ is n-butyl. The C-15 epimer of the compound named above (15-epi-3,7-inter-m-phenylene-3-oxa-4,5,6-trinor-$PGE_1$, amide) is represented above when the hydroxy of the $M_1$ moiety is in the beta configuration. See particularly, U.S. Ser. No. 614,242, filed Sept. 17, 1975, for description of the various conventions with respect to the stereochemistry at C-15 as employed herein.

In formula I above, as well as in formulas hereinafter, broken line attachments to the cyclopentane ring indicate substituents in "alpha" ($\alpha$) configuration i.e., below the plane of the cyclopentane ring. Heavy solid line attachments to the cyclopentane ring indicate substituents in "beta" ($\beta$) configuration, i.e., above the plane of the cyclopentane ring. The use of wavy lines ($\sim$) herein will represent attachment of substituents in either the alpha or beta configuration or attachment in a mixture of alpha and beta configurations.

The side-chain hydroxy at C-15 in the above formula I is in S or R configuration, as determined by the Cahn-Ingold-Prelog sequence rules. See J. Chem. Ed. 41: 16 (1964). See, also Nature 212, 38 (1966) for discussion of the stereochemistry of the prostaglandins. As used herein, expressions such as C-2, C-15, and the like, refer to the carbon atom in the prostaglandin analog which is in the position corresponding to the position of the same number in prostanoic acid.

Molecules of the known prostaglandins and asymmetric PG analogs each have several centers of asymmetry, and can exist in racemic (optically inactive) form and in either of the two enantiomeric (optically active) forms, i.e. the dextrorotatory and levorotatory forms. As drawn, the above formula I represents the particular optically active form of the prostaglandin analogs as claimed herein which corresponds to those stereoisomers of known prostaglandins as obtained from mammalian tissues, for example, sheep vesicular glands, swine lung, or human seminal plasma. In particular, refer to the stereoconfiguration at C-8 (alpha), C-11 (alpha), and C-12 (beta) of endogenously-produced $PGF_2\alpha$. The mirror image of the above formula I represents the other enantiomer of these prostaglandin analogs. The racemic form of such prostaglandin analogs contains equal numbers of both enantiomeric molecules, and the above formula I and the mirror image of that formula is needed to represent correctly the corresponding racemic prostaglandin analog.

For convenience hereinafter, use of the term, prostaglandin or "PG" will mean the optically active form of that prostaglandin thereby referred to with the same absolute configuration as $PGF_2\alpha$, obtained from mammalian tissues.

The term "prostaglandin-type" (PG-type) product, as used herein, refers to any cyclopentane derivative herein which is useful for at least one of the same pharmacological purposes as the prostaglandins.

The formulas, as drawn herein, which depict a prostaglandin-type product or an intermediate useful in preparing a prostaglandin-type compounds, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type products.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type product herein, the term prostaglandin analog refers to the compound of that formula or a mixture comprising that compound and the enantiomer thereof.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

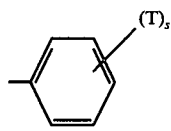

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-4-chloro-3-fluorophenyl, (3- or 4-(chloro-2-fluorophenyl, o-, m-, or p-trifluoromethylphenyl, (o-, m-, or p-)methoxyphenyl, (o-, m-, or p-)ethoxyphenyl, (4- or 5-)chloro-2-methylphenyl, and 2,4-dichloro(5- or 6-)methylphenyl.

Amides within the scope of alkylamino groups of the formula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and di-cyclohexylamide. Amides within the scope of aralkylamino are benzylamide, 2-phenylethylamide, 2-phenylethylamide, N-methyl-N-benzylamide, and dibenzylamide. Amides within the scope of substituted phenylamino are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanalide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylakllylamino are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridylethylamide, 4-chloro-β-pyridylethylamide, 4-methyl-α-pyridylpropylamide, 4-methyl-β-pyridylpropylamide, 4-chloro-pyridylpropylamide, 4- chloro-β-pyridylpropylamide, 4-methyl-62-pyridylbutylamide, 4-methyl-α-pyridylbutylamide, 4-chloropyridylbutylamide, 4-chloro-β-pyridylbutylamide, 4-methyl-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxyethylamide. Amides with the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)-1-hydroxyethylamide, α,α-dihydroxybutylamide, α,β-dihydroxybutylamide, α,γ-dihydrobutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide, Amides within the scope of trihydroxyalkylamino are tris(hydroxymethyl)methylamide and 1,3-dihydroxy-2-hydroxymethylpropylamide.

Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

Amides within the scope of carbonylamino of the formula —$NR_{23}COR_{21}$ are methylcarbonylamide, ethylcarbonylamide, phenylcarbonylamide, and benzylcarbonylamide. Amides within the scope of sulfonylamino of the formula —$NR_{23}SO_2R_{21}$ are methylsulfonylamide, ethylsulfonylamide, phenylsulfonylamide, p-tolylsulfonylamide, and benzylsulfonylamide.

Hydrazides within the scope of the above hydrazino groups are hydrazine, N-aminopiperidine, benzoylhydrazine, phenylhydrazine, N-aminomorpholine, 2-hydroxyethylhydazine, methylhydrazine, 2,2,2-hydroxyethylhydrazine and p-carboxyphenylhydrazine.

Within the scope of the novel PG-type carboxyamides described above, certain of these compounds are preferred in that they exhibit increased potency, duration or selectivity of action, provide more easily stabilized pharmacological formulations, or exhibit a decreased toxicity at the appropriate therapeutic or prophylactic dose. Accordingly, the preferred compounds herein include those compounds where the inter-phenylene moiety is incorporated into the carboxyamide-terminated side chain in the "meta" position. With further reference to the carboxyamide-terminated side chain, those compounds wherein g is 3 or 1, mose especially 1, are preferred.

In cases where increased pharmacological potency is desired, those compounds wherein the C-15 hydroxy is of the "alpha" configuration are especially preferred. With regard to the various substituents at C-15 and C-16, it is preferred that at least one of $R_3$, $R_4$, and $R_5$ be hydrogen. Further, in the event one of $R_3$ and $R_4$ is methyl or fluoro, it is preferred that $R_3$ and $R_4$ both be methyl or fluoro, respectively.

For those compounds herein where $Y_1$ is cis— CH═CH—, those compounds wherein $R_3$, $R_4$, and $R_5$ are all hydrogen are preferred.

For the ω-aryl ($R_7$ is aryl) compounds herein, preferred compounds are those wherein s is zero or one and T is chloro, fluoro or trifluoromethyl.

In employing the present compounds to product antithrombotic acitivity, especially preferred compounds are those substituted at C-9 or C-11 by oxo. Further, the especially preferred compounds for this purpose are those exhibiting the PGE- or 11-deoxy-PGE-type ring structure.

Regarding the nature of the C-2 substitution for the novel carboxyamides disclosed herein, the preferred amido substituents are those wherein $R_{21}$ and $R_{22}$ are preferably hydrogen or alkyl of 1 to 8 carbon atoms, inclusive, being the same or different, preferably with the total number of carbon atoms in $R_{21}$ and $R_{22}$ being less than or equal to 8. More especially preferred are those carboxyamide substituents wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to four.

For convenience in preparation and use, the amido group —$NH_2$ is most especially preferred.

With regard to the various cycloamino groups described above, preferred cycloamino groups are those wherein the $R_{21}$ and $R_{22}$ substituents represent the preferred values therefor as described for the acyclic amino groups above. Most preferably, $R_{21}$ and $R_{22}$ are both hydrogen.

With regard to the carbonylamino groups described above, $R_{23}$ is preferably hydrogen and $R_{21}$ is preferably alkyl of one to 8 carbon atoms, inclusive. More preferably, $R_{21}$ is alkyl of one to 4 carbon atoms, inclusive, especially being methyl. With regard to the sulfonylamino groups described above, $R_{21}$ and $R_{23}$ most preferably exhibit those preferred values as described for carbonylamino groups.

The present inter-phenylene-PG-type carboxyamides are prepared by amidization of corresponding PG-type free acids. Such free acids are themselves known or prepared by prior art methods, particularly being prepared by methods described in U.S. Pat. No. 3,933,898, German Offenlegungsschrift No. 2,635,838, or more preferably the process essentially described in APPENDIX I. attached hereto.

Having prepared the inter-phenylene-type PG carboxylic acids, the corresponding carboxyamides are prepared by one of several amidization methods known in the prior art. See, for example, U.S. Pat. No. 3,981,868, issued Sept. 21, 1976 for a description of the preparation of the present amino and cycloamino derivatives of prostaglandin-type free acids and U.S. Pat. No. 3,954,741 describing the preparation of carbonylamino and sulfonylamino derivatives of prostaglandin-type free acids.

The preferred method by which the present amino and cycloamino derivatives of the inter-phenylene-PG-type acids are prepared is, first, by transformation of such free acids to corresponding mixed acid anhydrides. By this procedure, the prostaglandin free acid is first neutralized with an equivalent of an amine base, and thereafter reacted a slight stoichiometric excess of an alkylchloroformate alkylsulphonyl chloride corresponding to the mixed anhydride to be prepared.

The amine base preferred for neutralization is triethylamine, although other amines (e.g. N-methylmorpholine, pyridine, N,N-diisopropylethylamine) are likewise employed. Further, a convenient, readily available alkylchloroformate or alkylsulfonyl chloride for use in the mixed anhydride production is isobutyl chloroformate or methanesulfonyl chloride.

The mixed anhydride formation proceeds by conventional methods and accordingly the inter-phenylene-PG-type free acid is mixed with both the tertiary amine base and the chloroformate or sulphonylchloride in a suitable solvent (e.g. acetone, tetrahydrofuran), allowing the reaction to proceed at $-10°$ to $20°$ C.

Thereafter, the mixed anhydride is converted to the corresponding amino or cycloamino derivative by reaction with the amine corresponding to the amide to be prepared. In the case where the simple amide ($-NH_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete. For highly volatile amines, acid addition salts thereof (e.g. methylamine hydrochloride) are employed in place of the corresponding free base (e.g. methylamine) with however the addition of pyridine.

Thereafter, the novel inter-phenylene-PG-type amino or cycloamido derivative is recovered from the reaction mixture by conventional techniques.

The carbonylamino and sulfonylamino derivatives of the presently claimed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl or sulfonyl isocyanate, corresponding to the carbonylamino or sulfonylamino derivative to be prepared.

By another, more preferred method the sulfonylamino derivatives of the present compounds are prepared by first generating the PG-type mixed anhydride, employing the method described above for the preparation of the amino and cycloamino derivatives. Thereafter, the sodium salt of the corresponding sulfonamide is reacted with the mixed anhydride and hexamethylphosphoramide. The pure PG-type sulfonylamino derivative is then obtained from the resulting reaction mixture by conventional techniques.

The sodium salt of the sulfonamide corresponding to the sulfonylamino derivative to be prepared is generated by reacting the sulfonamide with alcoholic sodium methoxide. Thus, by a preferred method methanolic sodium methoxide is reacted with an equal molar amount of the sulfonamide. The sulfonamide is then reacted, as described above, with the mixed anhydride, using about four equivalents of the sodium salt per equivalent of sulfonmide. Reaction temperatures at or about 0° C. are employed.

As indicated above, the novel prostaglandin carboxyamides of the present invention, especially the preferred compounds described herein, correspond to the previously known inter-phenylene-PG-type acids and esters, in that these novel prostaglandin carboxyamides exhibit the same prostaglandin-type biological activity as previously known for such acids and esters. Specifically, the present carboxyamides are useful for each of the known purposes for which the corresponding acids and esters are used, and, moreover, are used in the same manner as such acids and esters.

The previously known inter-phenylene-PG-type esters and acids are all potent in causing numerous biological responses at low dosages. Furthermore, these free acids and esters, while exhibiting substantial biological activity by numerous routes of administration, provided orally induced prostaglandin-type responses for inconveniently short durations.

In striking contrast, however, the novel prostaglandin carboxyamides of the present invention are substantially more useful with regard to orally induced biological responses, exhibiting a surprising and unexpected prolongation of prostaglandin-type activity by this method of administration. Moreover, this prolongation of oral activity is particularly and especially pronounced in the employment of the prostaglandin-type carboxamides of the present invention as antithrombotic agents.

The novel prostaglandin carboxamides of the present invention are thus surprisingly and unexpectedly more useful than the known correspond acids and esters as antithrombotic agents. In particular, the present carboxamides are useful, prolonged orally active agent to decrease blood platelet adhesion (as shown by plateletto glass adhesiveness) and inhibit blood platelet aggregation and thrombosis formation, as induced by various physical stimuli (e.g. arterial injury) or chemical stimuli (e.g. adenosine diphosphate, adenosine triphosphate, serotinin, thrombin and collagen).

Accordingly, the novel prostaglandin carboxyamides are useful whenever medical therapy requires a pharmacological agent to inhibit platelet aggregation, reduce the adhesive character of platelet or remove or prevent the formation of thrombi in mammals, including man, rabbits, and rats. For example, these compounds are useful in the treatment and prevention of myocardial infraction, post-operative thrombosis, and the maintenance of patency of vascular grafts following surgery. Moreover, these novel prostaglandin-type carboxyamides are useful to treat conditions such as atherosclerosis, arteriosclerosis, blood clotting defects due to lipemia and other clinical conditions in which the underlying etiology is associated with lipid imbalance or hyperlipidemia. For the purposes described above, the present prostaglandin-type carboxyamides are administered systemically, e.g. intravenously, subcutaneously, intramuscularly in the form of sterile implants for prolonged action. However, the surprising and unexpectedly prolonged oral activity of these compounds renders oral administration the preferred systemic route of administration.

For example, the carboxyamides are administered orally at a dose of about 1mg/kg of body weight, and the dosage is repeated at about 8 hour intervals. Alternatively dosages in the range of 0.1 to 20 mg/kg are employed with more or less frequent administration depending on whether the lower or higher dosage is used respectively. Thus at a dose of about 0.1 mg/kg dosages are repeated every 2-6 hours, while at dosages of 20 mg/kg activity up to about 12 hours is observed.

As with the corresponding acids and esters these compounds are formulated for pharmacological use by known, conventional methods.

DESCRIPTION OF THE PREFERRED EMBODIMENTS

The invention can be more fully understood by the following examples.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1

3,7-Inter-m-phenylene-3-oxa-4,5,6-trinor-PGE$_1$, amide (Formula I: L$_2$ is —NH$_2$, g is one, Z$_3$ is oxa and attached to the phenyl ring in the position meta to the methylene, D is a PGE-type cyclopentane ring, Y$_1$ is trans—CH=CH—, R$_3$, R$_4$, and R$_5$ are all hydrogen and the hydroxyl of M$_1$ is in the alpha configuration, and R$_7$ is n-butyl).

A solution of 6.24 mg. of 3,7-inter-m-phenylene-3-oxa-4,5,6-trinor-PGE$_1$ in 10 ml. of dry acetone is treated with 0.222 ml. of treithylamine. Under a nitrogen atmosphere this solution is cooled to −10° C. and 0.209 ml. of isobutylchloroformate is added.

After 8 min. of maintaining a reaction temperature of −5° to 0° C., the resulting mixture is treated with a 10 ml. solution of acetonitrile which is saturated (at ambient temperature) with anhydrous ammonia. About 20 mmoles of ammonia is present in the mixture.

After a further reaction of 10 min. at ambient temperature, the reaction mixture is then filtered to remove the precipitate and evaporation of the filtrate under reduced pressure at 45° C. yield a viscous residue. This residue is chromatographed on silica gel eluting with a mixture of acetonitrile and tetrahydrofuran (7:3). Concentration of the reduced pressure yields 600 mg. of crude solid product. The crude product is then dissolved in 5 ml. of ethyl acetate and allowed to form a gelatinous mass by cooling to −5° to 0° C. for 12 hours. This gelatinous solid is then mixed with 10 m. of hexane. A white solid is formed which is recovered by filtration under a nitrogen atmosphere, which is the pure title product. Silica gel TLC R$_f$ is 0.6 in an acetonitrile and tetrahydrofuran (7:3) mixture. About 375 mg. of white free flowing crystalline product is obtained. The title product exhibits the following elemental analysis: carbon (64.64%), hydrogen (8.15%), and nitrogen (3.55%). The melting point is observed to be in the range of 65.9° to 73.2° C.

EXAMPLE 2

3,7-Inter-m-phenylene-3-oxa-4,5,6-trinor-11-deoxy-13,14-didehydro-PGE$_1$, amide (Formula I: L$_2$ is —NH$_2$, g is one, Z$_3$ is oxa and attached to the phenyl ring in the position meta to the methylene, is an 11-deoxy-PGE-type cyclopentane ring, Y$_1$ is —CH$_2$CH$_2$—, R$_3$, R$_4$, and R$_5$ are all hydrogen and the hydroxy of the M$_1$ moiety is in the alpha configuration, and R$_7$ is n-butyl).

A solution of 200 mg. of 3,7-inter-m-phenylene-3-oxa-4,5,6-trinor-13,14-dihydro-11-deoxy-PGE$_1$ in four ml. of dry acetone is cooled to −25° C. and treated with 0.074 ml. of triethylamine.

After stirring the resulting mixture at −25° to −15° C. for 15 min., 0.068 ml. of isobutylchloroformate is added. Stirring is continued at −15° to 0° C. for 30 min.

This reaction mixture is then treated with four ml. of acetonitrile saturated with ammonia (at ambient temperature). After 30 additional min., the resulting mixture is then filtered, washing well with ethyl acetate. The filtrate is then concentrated under reduced pressure to yield 0.25 g. of crude product. Chromatographing on silica gel, eluting with a mixture of actone and methylene chloride (1:9), yields 0.17 g. of pure title product as an oil. NMR absorptions are observed at 0.88, 0.831, 4.47, and 6.5 to 7.42 delta. Infrared absorptions are observed at 34.20, 17.35, 16.90, 16.05, 15.85, 14.90, 12.65, 11.60, 10,65, 7.85 and 6.95 cm$^{-1}$. The mass spectrum of the bis(trimethylsilyl) derivative exhibits a high resolution peak at 519.3193 and other peaks at 504, 448, 429, 414, and 173. The silica gel TLC R$_f$ is 0.26 in the A-IX solvent system. The silica gel TLC R$_f$ is 0.19 in a mixture of acetone and methylene chloride (3:7).

Following the procedure described above, there are prepared PG-type amides of the PGFα, 11-deoxy-PGFα, PGE, 11-deoxy-PGE, PGD, 9-deoxy-PGD, 9-deoxy-9,10-didehydro-PGD, or PGA-type, and corresponding 15-epimers, exhibiting the following side chain modifications:

3,7-Inter-m-phenylene-3-oxa-4,5,6-trinor-;
3,7-Inter-m-phenylene-3-oxa-4,5,6-trinor-16-methyl-;
3,7-Inter-m-phenylene-3-oxa-4,5,6-trinor-16,16-dimethyl-;
3,7-Inter-m-phenylene-3-oxa-4,5,6-trinor-16-fluoro-;
3,7-Inter-m-phenylene-3-oxa-4,5,6-trinor-16,16-difluoro-;
3,7-Inter-m-phenylene-3-oxa-17-phenyl-4,5,6,18,19,20-hexanor-;
3,7-Inter-m-phenylene-3-oxa-17-(m-trifluoromethylphenyl)-4,5,6,18,19,20-hexanor-;
3,7-Inter-m-phenylene-3-oxa-17-(m-chlorophenyl)-4,5,6,18,19,20-hexanor-;
3,7-Inter-m-phenylene-3-oxa-17-(p-fluorophenyl)-4,5,6,18,19,20-hexanor-;
3,7-Inter-m-phenylene-3-oxa-16-methyl-17-phenyl-4,5,6,18,19,20-hexanor-;
3,7-Inter-m-phenylene-3-oxa-16,16-dimethyl-17-phenyl-4,5,6,18,19,20-hexanor-;
3,7-Inter-m-phenylene-3-oxa-16-fluoro-17-phenyl-4,5,6,18,19,20-hexanor-;
3,7-Inter-m-phenylene-3-oxa-16,16-difluoro-17-phenyl-4,5,6,18,19,20-hexanor-;

3,7-Inter-m-phenylene-3-oxa-16-phenoxy-4,5,6,17,18,19,20-heptanor-;
3,7-Inter-m-phenylene-3-oxa-16-(m-trifluoromethylphenoxy)-4,5,6,17,18,19,20-heptanor-;
3,7-Inter-m-phenylene-3-oxa-16-(m-chlorophenoxy)-4,5,6,17,18,19,20-heptanor-;
3,7-Inter-m-phenylene-3-oxa-4,5,6-trinor-16-(p-fluorophenoxy)-4,5,6,17,18,19,20-heptanor-;
3,7-Inter-m-phenylene-3-oxa-16-phenoxy-4,5,6,18,19,20-hexanor-;
3,7-Inter-m-phenylene-3-oxa-4,5,6-trinor-16-methyl-16-phenoxy-4,5,6,18,19,20-hexanor-;
3,7-Inter-m-phenylene-3-oxa-4,5,6-trinor-13,14-dihydro-;
3,7-Inter-m-phenylene-3-oxa-4,5,6-trinor-16-methyl-13,14-dihydro-;
3,7-Inter-m-phenylene-3-oxa-4,5,6-trinor-16,16-dimethyl-13,14-dihydro-;
3,7-Inter-m-phenylene-3-oxa-4,5,6-trinor-16-fluoro-13,14-dihydro-;
3,7-Inter-m-phenylene-3-oxa-4,5,6-trinor-16,16-difluoro-13,14-dihydro-;
3,7-Inter-m-phenylene-3-oxa-17-phenyl-4,5,6,18,19,20-trinor-13,14-dihydro-;
3,7-Inter-m-phenylene-3-oxa-17-(m-trifluoromethylphenyl)-4,5,6,18,19,20-hexanor-13,14-dihydro-;
3,7-Inter-m-phenylene-3-oxa-17-(m-chlorophenyl)-4,5,6,18,19,20-hexanor-13,14-dihydro-;
3,7-Inter-m-phenylene-3-oxa-17-(p-fluorophenyl)-4,5,6,18,19,20-hexanor-13,14-dihydro-;
3,7-Inter-m-phenylene-3-oxa-16-methyl-17-phenyl-4,5,6,18,19,20-hexanor-13,14-dihydro-;
3,7-Inter-m-phenylene-3-oxa-16,16-dimethyl-17-phenyl-4,5,6,18,19,20-hexanor-13,14-dihydro-;
3,7-Inter-m-phenylene-3-oxa-16-fluoro-17-phenyl-4,5,6,18,19,20-hexanor-13,14-dihydro-;
3,7-Inter-m-phenylene-3-oxa-16,16-difluoro-17-phenyl-4,5,6,18,19,20-hexanor-13,14-dihydro-;
3,7-Inter-m-phenylene-3-oxa-16-phenoxy-4,5,6,17,18,19,20-heptanor-13,14-dihydro-;
3,7-Inter-m-phenylene-3-oxa-16-(m-trifluoromethylphenoxy)-4,5,6,17,18,19,20-heptanor-13,14-dihydro-;
3,7-Inter-m-phenylene-3-oxa-16-(m-chlorophenoxy)-4,5,6,17,18,19,20-heptanor-13,14-dihydro-;
3,7-Inter-m-phenylene-3-oxa-16-(p-fluorophenoxy)-4,5,6,17,18,19,20-heptanor-13,14-dihydro-;
3,7-Inter-m-phenylene-3-oxa-16-phenoxy-4,5,6,18,19,20-hexanor-13,14-dihydro-;
3,7-Inter-m-phenylene-3-oxa-16-methyl-16-phenoxy-4,5,6,18,19,20-hexanor-13,14-dihydro-;
3,7-Inter-m-phenylene-4,5,6-trinor-;
3,7-Inter-m-phenylene-4,5,6-trinor-16-methyl-;
3,7-Inter-m-phenylene-4,5,6-trinor-16,16-dimethyl-;
3,7-Inter-m-phenylene-4,5,6-trinor-16-fluoro-;
3,7-Inter-m-phenylene-4,5,6-trinor-16,16-difluoro-;
3,7-Inter-m-phenylene-17-phenyl-4,5,6,18,19,20-hexanor-;
3,7-Inter-m-phenylene-17-(m-trifluoromethylphenyl)-4,5,6,18,19,20-hexanor-;
3,7-Inter-m-phenylene-17-(m-chlorophenyl)-4,5,6,18,19,20-hexanor-;
3,7-Inter-m-phenylene-17-(p-fluorophenyl)-4,5,6,18,19,20-hexanor-;
3,7-Inter-m-phenylene-16-methyl-17-phenyl-4,5,6,18,19,20-hexanor-;
3,7-Inter-m-phenylene-16,16-dimethyl-17-phenyl-4,5,6,18,19,20-hexanor-;
3,7-Inter-m-phenylene-16-fluoro-17-phenyl-4,5,6,18,19,20-hexanor-;
3,7-Inter-m-phenylene-16,16-difluoro-17-phenyl-4,5,6,18,19,20-hexanor-;
3,7-Inter-m-phenylene-16-phenoxy-17-phenyl-4,5,6,18,19,20-heptanor-;
3,7-Inter-m-phenylene-16-(m-trifluoromethylphenoxy)-4,5,6,17,18,19,20-heptanor-;
3,7-Inter-m-phenylene-16-(m-chlorophenoxy)-4,5,6,17,18,19,20-heptanor-;
3,7-Inter-m-phenylene-16-(p-fluorophenoxy)-4,5,6,17,18,19,20-heptanor-;
3,7-Inter-m-phenylene-16-phenoxy-4,5,6,18,19,20-hexanor-;
3,7-Inter-m-phenylene-16-methyl-16-phenoxy-4,5,6,18,19,20-hexanor-;
3,7-Inter-m-phenylene-4,5,6-trinor-13,14-dihydro-;
3,7-Inter-m-phenylene-4,5,6-trinor-16-methyl-13,14-dihydro-;
3,7-Inter-m-phenylene-4,5,6-trinor-16,16-dimethyl-13,14-dihydro-;
3,7-Inter-m-phenylene-4,5,6-trinor-16-fluoro-13,14-dihydro-;
3,7-Inter-m-phenylene-4,5,6-trinor-16,16-difluoro-13,14-dihydro-;
3,7-Inter-m-phenylene-17-phenyl-4,5,6,18,19,20-hexanor-13,14-dihydro-;
3,7-Inter-m-phenylene-17-(m-trifluoromethylphenyl)-4,5,6,18,19,20-hexanor-13,14-dihydro-;
3,7-Inter-m-phenylene-17-(m-chlorophenyl)-4,5,6,18,19,20-hexanor-13,14-dihydro-;
3,7-Inter-m-phenylene-17-(p-fluorophenyl)-4,5,6,18,19,20-hexanor-13,14-dihydro-;
3,7-Inter-m-phenylene-16-methyl--17-phenyl-4,5,6,18,19,20-hexanor-13,14-dihydro-;
3,7-Inter-m-phenylene-16,16-dimethyl-17-phenyl-4,5,6,18,19,20-hexanor-13,14-dihydro-;
3.7-Inter-m-phenylene-16-fluoro-17-phenyl-4,5,6,18,19,20-hexanor-13,14-dihydro-;
3,7-Inter-m-phenylene-16,16-difluoro-17-phenyl-4,5,6,18,19,20-hexanor-13,14-dihydro-;
3,7-Inter-m-phenylene-16-phenoxy-4,5,6,17,18,19,20-heptanor-13,14-dihydro-;
3,7-Inter-m-phenylene-16-(m-trifluoromethylphenoxy)-4,5,6,17,18,19,20-heptanor-13,14-dihydro-;
3,7-Inter-m-phenylene-16-(m-chlorophenoxy)-4,5,6,17,18,19,20-heptanor, 13,14-dihydro-;
3,7-Inter-m-phenylene-16-(p-fluorophenoxy)-4,5,6,17,18,19,20-heptanor-13,14-dihydro-;
3,7-Inter-m-phenylene-16-phenoxy-4,5,6,18,19,20-hexanor-13,14-dihydro-;
3,7-Inter-m-phenylene-16-methyl-16-phenoxy-4,5,6,18,19,20-hexanor-13,14-dihydro-;
3,7-Inter-m-phenylene-3-oxa-4,5,6-trinor-cis-13-;
3,7-Inter-m-phenylene-3-oxa-4,5,6-trinor-16-methyl-cis-13-;
3,7-Inter-m-phenylene-3-oxa-4,5,6-trinor-16,16-dimethyl-cis-13-;
3,7-Inter-m-phenylene-3-oxa-4,5,6-trinor-16-fluoro-cis-13-;
3,7-Inter-m-phenylene-3-oxa-4,5,6-trinor-16,16-difluoro-cis-13-;
3,7-Inter-m-phenylene-3-oxa-17-phenyl-4,5,6,18,19,20-hexanor-cis-13-;
3,7-Inter-m-phenylene-3-oxa-17-(m-trifluoromethylphenyl)-4,5,6,18,19,20-hexanor-cis-13-;

3,7-Inter-m-phenylene-3-oxa-17-(m-chlorophenyl)-4,5,6,18,19,20-hexanor-cis-13-;
3,7-Inter-m-phenylene-3-oxa-17-(p-fluorophenyl)-4,5,6,18,19,20-hexanor-cis-13-;
3,7-Inter-m-phenylene-3-oxa-16-methyl-17-phenyl-4,5,6,18,19,20-hexanor-cis-13-;
3,7-Inter-m-phenylene-3-oxa-16,16-dimethyl-17-phenyl-4,5,6,18,19,20-hexanor-cis-13-;
3,7-Inter-m-phenylene-3-oxa-16-fluoro-17-phenyl-4,5,6,18,19,20-hexanor-cis-13-;
3,7-Inter-m-phenylene-3-oxa-16,16-difluoro-17-phenyl-4,5,6,18,19,20-hexanor-cis-13-;
3,7-Inter-m-phenylene-3-oxa-16-phenoxy-4,5,6,17,18,19,20-heptanor-cis-13-;
3,7-Inter-,-phenylene-3-oxa-16-(m-trifluoromethylphenoxy)-4,5,6,17,18,19,20-heptanor-cis-13-;
3,7-Inter-m-phenylene-3-oxa-16-(m-chlorophenoxy)-4,5,6,17,18,19,20-heptanor-cis-13-;
3,7-Inter-m-phenylene-3-oxa-4,5,6-trinor-16-(p-fluorophenoxy)-4,5,6,17,18,19,20-heptanor-cis-13-;
3,7-Inter-m-phenylene-3-oxa-16-phenoxy-4,5,6,18,19,20-hexanor-cis-13-;
3,7-Inter-m-phenylene-3-oxa-4,5,6-trinor-16-methyl-16-phenoxy-4,5,6,18,19,20-hexanor-cis-13-;
3,7-Inter-m-phenylene-4,5,6-trinor-cis-13-;
3,7-Inter-m-phenylene-4,5,6-trinor-16-methyl:cis-13-;
3,7-Inter-m-phenylene-4,5,6-trinor-16,16-dimethyl-cis-13-;
3,7-Inter-m-phenylene-4,5,6-trinor-16-fluoro-cis-13-;
3,7-Inter-m-phenylene-4,5,6-trinor-16,16-difluoro-cis-13-;
3,7-Inter-m-phenylene-17-phenyl-4,5,6,18,19,20-hexanor-cis-13-;
3,7-Inter-m-phenylene-17-(m-trifluoromethylphenyl)-4,5,6,18,19,20-hexanor-cis-13-;
3,7-Inter-m-phenylene-17-(m-chlorophenyl)-4,5,6,18,19,20-hexanor-cis-13-;
3,7-Inter-m-phenylene-17-(p-fluorophenyl)-4,5,6,18,19,20-hexanor-cis-13-;
3,7-Inter-m-phenylene-16-methyl-17-phenyl-4,5,6,18,19,20-hexanor-cis- 13-;
3,7-Inter-m-phenylene-16,16-dimethyl-17-phenyl-4,5,6,18,19,20-hexanor-cis-13-;
3,7-Inter-m-phenylene-16-fluoro-17-phenyl-4,5,6,18,19,20-hexanor-cis-13-;
3,7-Inter-m-phenylene-16,16-difluoro-17-phenyl-4,5,6,18,19,20-hexanor-cis-13-;
3,7-Inter-m-phenylene-16-phenoxy-17-phenyl-4,5,6,18,19,20-heptanor-cis-13-;
3,7-Inter-m-phenylene-16-(m-trifluoromethylphenoxy)-4,5,6,17,18,19,20-heptanor-cis-13-;
3,7-Inter-m-phenylene-16-(m-chlorophenoxy)-4,5,6,17,18,19,20-heptanor-cis-13-;
3,7-Inter-m-phenylene-16-(p-fluorophenoxy)-4,5,6,17,18,19,20- heptanor-cis-13-;
3,7-Inter-m-phenylene-16-phenoxy-4,5,6,18,19,20-hexanor-cis-13-;
3,7-Inter-m-phenylene-16-methyl-16-phenoxy-4,5,6,18,19,20-hexanor-cis-13-.

EXAMPLE 3

3,7-Inter-m-phenylene-3-oxa-4,5,6-trinor-PGE$_1$, methylsulfonylamide (Formula I: L$_2$ is —NHSO$_2$CH$_3$, g, Z$_3$, D, Y$_1$, R$_3$, R$_4$, R$_5$, and R$_7$ are as defined in Example 1).

A. The sodium salt of methylsulfonylamide is prepared by addition of 10 ml. of 4.4 N methanolic sodium methoxide to a mixture of 4.76 g. of methylsulfonylamide in 15 ml. of methanol. This mixture is then concentrated under reduced pressure and 40 ml. of benzene is added to the residue. Further concentration under reduced pressure yields the sodium salt, which is employed in part B without further purification.

B. To a solution of 3.5 g. of 3,7-inter-phenylene-3-oxa-4,5,6-trinor-PGE$_1$ in 50 ml. of dry dimethylformamide and 1.1 g. of triethylamine is added with stirring 1.50 g. of isobutyl chloroformate over a 5 min. period. The mixture is then stirred at 0° C. for 30 min. and the sodium salt prepared in part A is added. The resulting mixture is then combined with 10 ml. of dry hexamethylphosphoramide. The resulting mixture is then stirred for 12 hours at ambient temperature and thereafter acidified with cold dilute hydrochloric acic and extracted with ethyl acetate. The organic extract is then washed with water, brine and dried over magnesium sulfate. After concentrating under reduced pressure, the residue obtained is pure title product.

Following the procedure of Example 3, there are obtained each of the various inter-phenylene-PG-type compounds described following Example 2.

EXAMPLE 4

3,7-Inter-m-phenylene-3-oxa-4,5,6-trinor-PGE$_2$, methylamide (Formula I: L$_2$ is —NHCH$_3$, g, Z$_3$, D, Y$_1$, R$_3$, R$_4$, R$_5$, and R$_7$ are as defined in Example 1).

A solution of 1 g. of 3,7-inter-m-phenylene-3-oxa-4,5,6-trinor-PGE$_1$ in 10 ml. of dry acetone is treated with 0.5 ml. of triethylamine. Under a nitrogen atmosphere, this solution is cooled to −10° C. and 0.5 ml. of isobutylchloroformate is added. Afer six min. at −5° to 0° C. a solution of 600 ml. of methylamine hydrochloride and 5 ml. of dry pyridine is added. After 15 minutes at ambient temperature, the reaction mixture is diluted with 100 ml. of ethyl acetate and extracted with citric acid and phosphoric acid. The organic phase is then dried over sodium sulfate and solvent removed under reduced pressure. Cruce title product is then purified chromatographicaly, yielding pure title product.

Following the procedure described in Example 4, but employing dimethylamine in place of methylamine hydrochloride, there is obtained a corresponding diethylamide.

Following the procedure of Example 4, but employing ethylamine, isopropylamine, n-propylamine, n-butylamine, isobutylamine, t-butylamine, or n-pentylamine, in place of methylamine hydrochloride, there is obtained the corresponding amides.

Further following the procedure of Example 4, but employing piperidine, there is obtained the corresponding piperidylamide.

APPENDIX I

BACKGROUND OF THE INVENTION

This invention relates to intermediates useful in the preparation of prostaglandin analogs and to a process for preparing them.

Each of the known prostaglandins is a derivative of prostanoic acid which has the following structure and atom numbering:

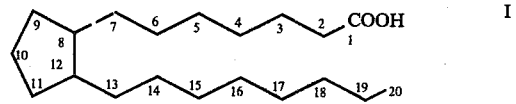

A systematic name of prostanoic acid is 7-[(2β-octyl)cyclopent-1α-yl]heptanoic acid.

Prostaglandin E₁, "PGE₁", has the following structure:

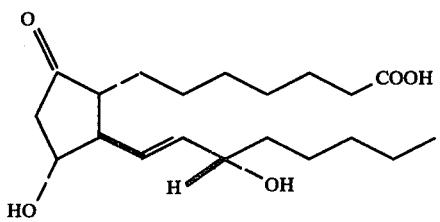

Prostaglandin F₁α, "PGF₁α", has the following structure:

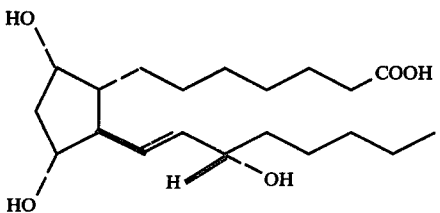

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the other enantiomeric form of that prostaglandin. The racemic form of the prostaglandins consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cylclopentane ring. Heavy solid line attachments to the cyclopentane ring indicate substituents in beta configuration, i.e., above the plane of the cyclopentane ring. In the formulas above, the hydroxyl attachment to carbon 15 is in the alpha configuration, as indicated by the broken line. In formulas below, this convention is also used for intermediates having hydroxyl substituted at the corresponding position on the side chain. A wavy line ~ indicates attachment to the side chain in alpha or beta configuration.

The various optically active and racemic prostaglandins and their alkyl esters are useful for various pharmacological purposes. With particular regard to PGF₁α see, for example, Bergstrom et al., Pharmacol. Rev. 20, 1 (1968), and references cited therein. As to the other prostaglandins, see, for example, Ramwell et al., Nature 221, 1251 (1969).

A group of prostaglandin analogs having a divalent phenylene moiety in the carboxyl-terminated side chain of the prostanoic acid structure (I) was disclosed in a pending United States patent application by Norman A. Nelson, Ser. No. 604,158, filed Aug. 13, 1975.

Included among those phenylene prostaglandin analogs were compounds represented by the formulas:

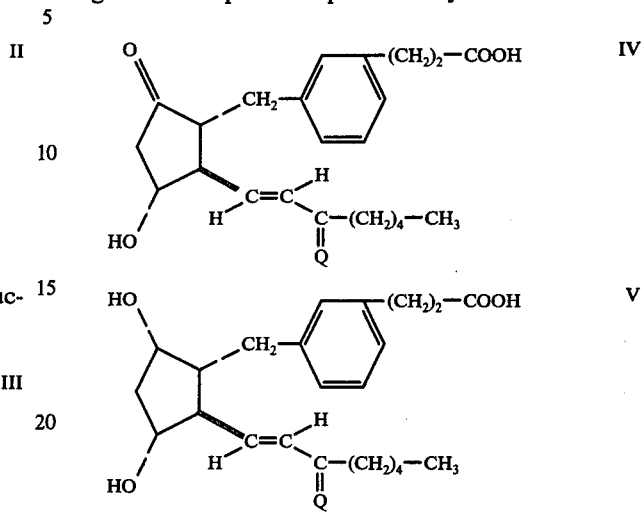

wherein Q is

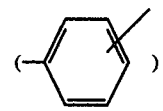

and R₁ is hydrogen or alkyl of one to 4 carbon atoms, inclusive.

Previously, certain prostaglandin analogs having an oxa oxygen (-O-) and a divalent phenylene moiety

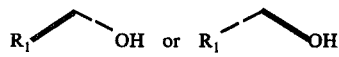

in the carboxyl-terminated side chain of the prostanoic acid structure (I) were disclosed. See U.S. Pat. No. 3,933,898.

Included among those phenylene-oxa prostaglandin analogs were compounds represented by the formulas:

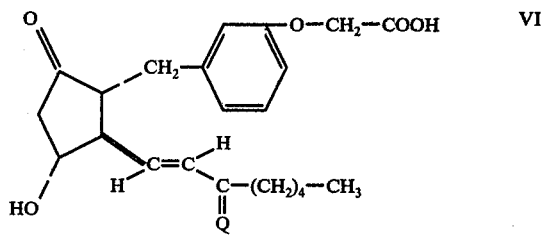

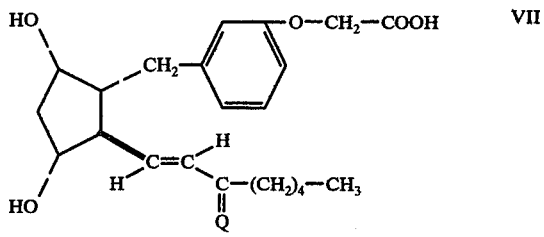

wherein Q is as defined above.

Each of the phenylene and phenylene-oxa prostaglandin analogs is useful in place of the corresponding known prostaglandins for at least one of their known pharmacological purposes, which include reduction of gastric secretion, inhibition of blood platelet aggregation, increase of nasal patency, and labor inducement at term.

SUMMARY OF THE INVENTION

It is the purpose of this invention to provide intermediates useful in the preparation of phenylene and phenylene-oxa prostaglandin analogs. It is a further purpose to provide novel processes for preparing these intermediates.

Accordingly, there are provided methyleneacyclopentane derivatives of the formula

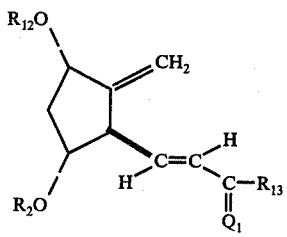
VIII wherein $Q_1$ is

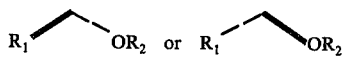

wherein $R_1$ is hydrogen or alkyl of one to 4 carbon atoms, inclusive; wherein $R_2$ is a blocking group including tetrahydropyranyl, tetrahydrofuranyl, 1-ethoxyethyl, or a group of the formula

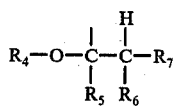

wherein $R_4$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_5$ and $R_6$ are the same or different, being hydrogen, alkyl of one to 4 carbon atoms, inclusive, phenyl or phenyl substituted with one, 2, or 3 alkyl of one to 4 carbon atoms, inclusive, or, when $R_5$ and $R_6$ are taken together, $-(CH_2)_a-$ or $-(CH_2)_b-O-(CH_2)_c-$ wherein $a$ is 3, 4, or 5, $b$ is one, 2, or 3, and $c$ is one, 2, or 3 with the proviso that $b$ plus $c$ is 2, 3, or 4, and wherein $R_7$ is hydrogen or phenyl; wherein $R_{12}$ is (1) hydrogen; (2) silyl of the formula $-Si(A)_3$ wherein A is alkyl of one to 4 carbon atoms, inclusive, phenyl, phenyl substituted with one to 2 fluoro, chloro, or alkyl of one to 4 carbon atoms, inclusive, or aralkyl of 7 to 12 carbon atoms, inclusive, the A groups being the same or different; or (3) carboxyacyl of the formula

wherein $R_9$ is hydrogen, alkyl of one to 19 carbon atoms, inclusive, or aralkyl or 7 to 12 carbon atoms, inclusive, wherein alkyl or aralkyl are substituted with zero to 3 halo atoms; and wherein $R_{13}$ is

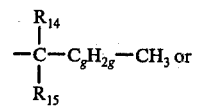
(1)

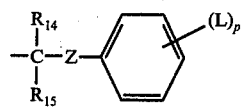
(2)

wherein $C_gH_{2g}$ is alkylene of one to 9 carbon atoms, inclusive, with one to 5 carbon atoms, inclusive, in the chain between $-CR_{14}R_{15}-$ and terminal methyl, wherein $R_{14}$ and $R_{15}$ are hydrogen, alkyl or one to 4 carbon atoms, inclusive, or fluoro, being the same or different, with the proviso that one of $R_{14}$ and $R_{15}$ is fluoro only when the other is hydrogen or fluoro and the further proviso that neither $R_{14}$ nor $R_{15}$ is fluoro when Z is oxa ($-O-$); wherein Z represents an oxa atom ($-O-$) or $C_jH_{2j}$ wherein $C_jH_{2j}$ is a valence bond or alkylene of one to 9 carbon atoms, inclusive, with one to 6 carbon atoms, inclusive betweeen $CR_{14}R_{15}-$ and the phenyl ring; and wherein L is alkyl of one to 4 carbon atoms, inclusive, fluoro, chloro, trifluoromethyl, or $-OR_{16}-$ wherein $R_{16}$ is alkyl of one to 4 carbon atoms, inclusive, and p is zero, one, 2 or 3, with the proviso that nor more than two L's are other than alkyl and when p is 2 or 3 the L's are either the same or different.

There are further provided substituted cyclopentanone derivatives of the formula

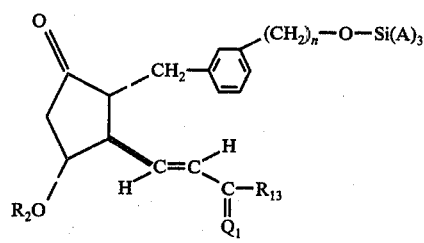
IX wherein A, $Q_1$, $R_2$ and $R_{13}$ are as defined above and wherein "n" is zero or 3, and a process for preparing those cyclopentanone derivatives by (a) oxidizing a compound of the formula

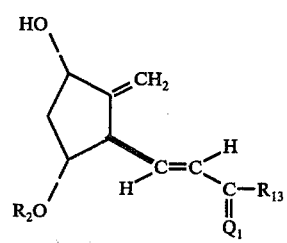
X wherein $Q_1$, $R_2$, and $R_{13}$ are as defined above, to form an enone of the formula

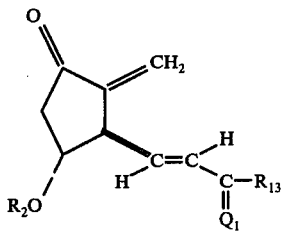

XI and (b) subjecting that enone to conjugative addition with a lithium diaryl cuprate reactant prepared from

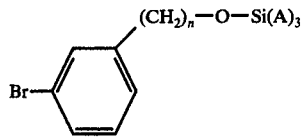

wherein A and "n" are as defined above.

With regard to formulas IV to XI, examples of alkyl of one to 4 carbon atoms, inclusive, are methyl, ethyl, propyl, butyl, and isomeric forms thereof. Examples of alkyl of one to 18 carbon atoms, inclusive, are those given above, and pentyl, hexyl, heptyl, octyl, nonyl, decyl, undecyl, dodecyl, tridecyl, tetradecyl, pentadecyl, hexadecyl, octadecyl and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-nahthylmethyl), Examples of phenyl substituted by one to 3 chloro or alkyl of one to 4 carbon atoms, inclusive, are (o-, m-, or p-)chlorophenyl, 2,4-dichlorophenyl, 2,4,6-trichlorophenyl, (o-, m-, or p-)tolyl, p-ethylphenyl, p-tert-butylphenyl, 2,5-dimethylphenyl, 4-chloro-2-methylphenyl, and 2,4-dichloro-3-methylphenyl.

Examples of alkylene of one to 9 carbon atoms, inclusive with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH₃)—, —C(CH₃)₂—, —CH(CH₂CH₃)—, —CH₂—CH(CH₃)—, —CH(CH₃)—CH(CH₃)—, —CH₂—C(CH₃)₂—, —CH₂—CH(CH₃)—CH₃, —CH₂—CH₂—CH(CH₂CH₂CH₃)—, —CH(CH₃)—CH(CH₃)—CH₂—CH₂—, —CH₂—CH₂—CH₂—C(CH₃)₂-CH₂, and —CH₂—CH₂—CH₂—CH₂—CH(CH₃)—. Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_gH_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH₂—, —CHF—CHF—, —CH₂—CH₂—CF₂—, —CH₂—CHF—CH₂—, —CH₂—CH₂CF(CH₃)—, —CH₂—CH₂—CF₂—CH₂—, —CH(CH₃)—CH₂—CH₂—CHF—, —CH₂—CH₂—CH₂—CH₂—CF₂—, —CHF—CH₂—CH₂—CH₂—CH₂—, —CF₂—CH₂—CH₂—CH₂—CH₂—, —CH₂—CH₂—CH₂—CH₂—CF₂—CH₂—CH₂—, and —CH₂—CH₂—CH₂—CH₂—CF₂.

Examples of

as defined above are
phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α, α, α-trifluoro-(o-, m-, or p-)tolyl,
(o-, m-, or p-)methoxyphenyl,
(o-, m-, or p-)ethoxyphenyl,
(4- or 5-)chloro-2-methoxyphenyl, and
2,4-dichloro(5- or 6-)methoxyphenyl.

Reference to Charts A, B, and C, herein, will make clear the steps by which the above novel intermediates are prepared and utilized in preparing the phenylene and phenylene-oxa prostaglandin analogs.

In Chart A, steps to the formula-X and-XI compounds are shown, together with steps leading to phenylene products of formula IV. In Chart A, the terms A, Q, $Q_1$, and $R_2$ are as defined above.

The bicyclic lactone starting reactants of formula XII are known in the art or are available by processes known in the art. For example, when $R_{13}$ is —(CH₂)₄—CH₃, and Q is

see Corey et al., J. Am. Chem. Soc. 92, 397 (1970). For other XII lactones see, for example, U.S. Pat. Nos. 3,903,131, 3,967,293, 3,987,087, and British specification cited in Derwent Farmdoc No. 73279U. See especially U.S. Pat. No. 3,931,279 issued to N.A. Nelson, particularly columns 27-34, which are incorporated herein by reference.

In step (a) of Chart A, the formula-XIII blocked lactones are formed from reactants XII by methods described herein or known in the art.

When the blocking group $R_2$ is tetrahydropyranyl or tetrahydrofuranyl, the appropriate reagent, e.g. 2,3-dihydropyran or 2,3-dihydrofuran, is used in an inert solvent such

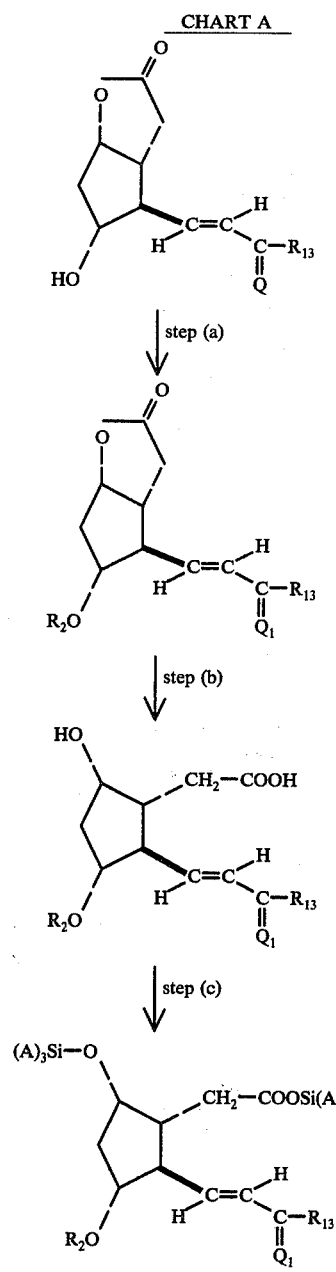

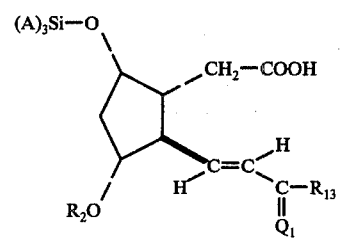

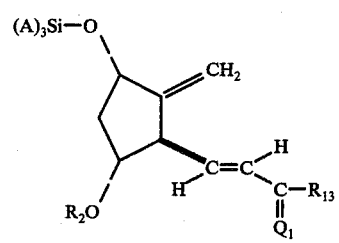

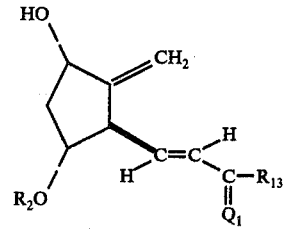

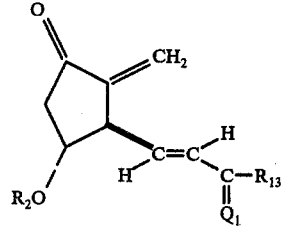

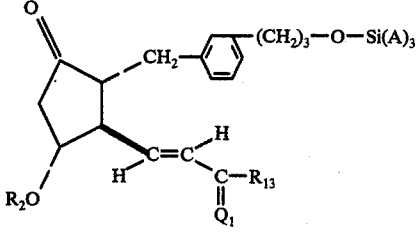

-continued
CHART A
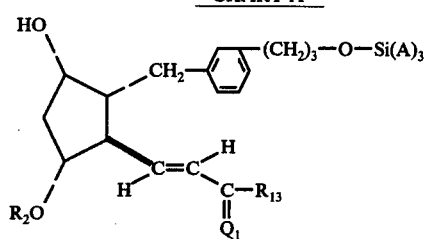
XIX
step (j)
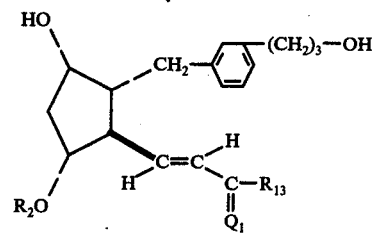
XX
step (k)
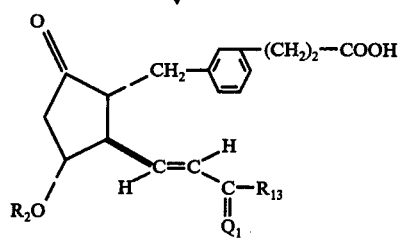
XXI
step (l)
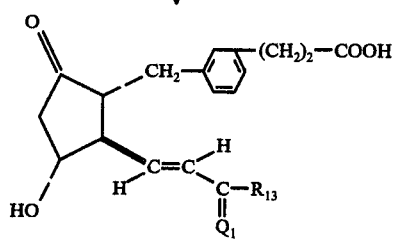
XL
CHART B
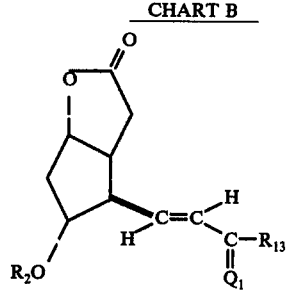
XIII
(a)
-continued
CHART B
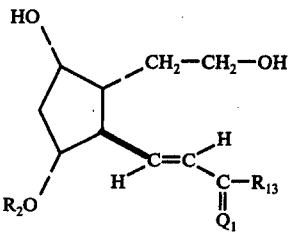
XXII
(b)
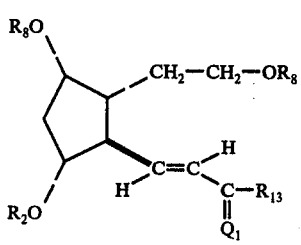
XXIII
(c)
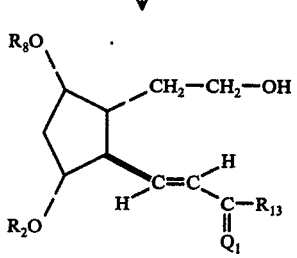
XXIV
(d)
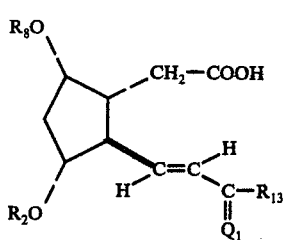
XXV
(e)
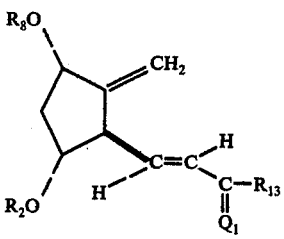
XXVI
(f)

-continued
CHART B
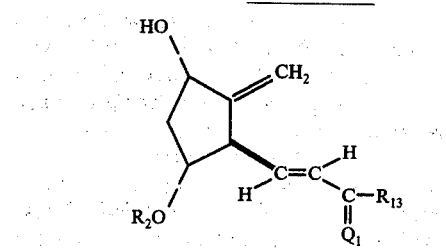
CHART C
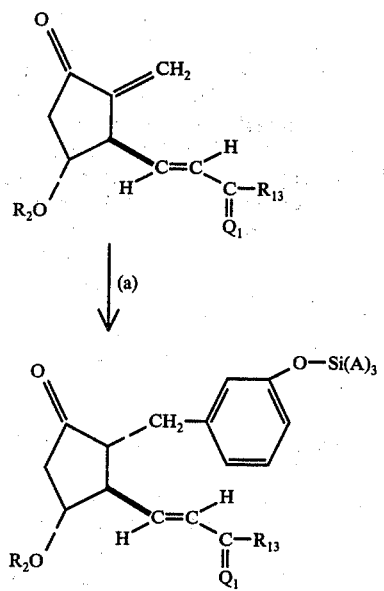
-continued
CHART C
   XXX
   XXXI
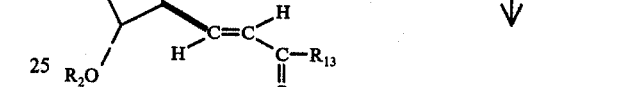   XXVII
   XXXII
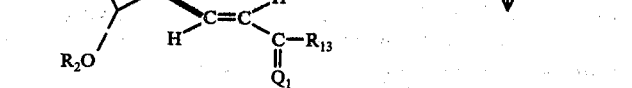   XXVIII
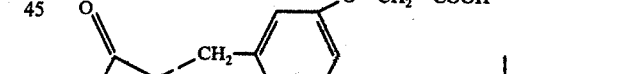   XXXIII
   XXIX
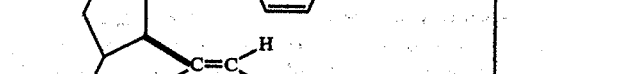   XLI -continued
CHART C

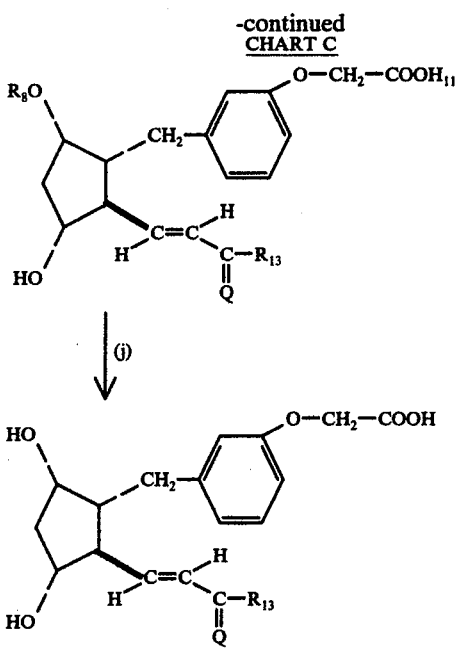

as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

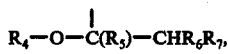

as defined above, the appropriate reagent is a vinyl ether, e.g., isobutyl vinyl ether or any vinyl ether of the formula $R_4$—O—$C(R_5)$=$CR_6R_7$ wherein $R_4$, $R_5$, $R_6$, and $R_7$ are as defined above; or an unsaturated cyclic or heterocyclic compound, e.g. 1-cyclohex-1-yl methyl ether

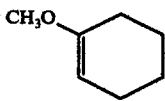

or 5,6-dihydro-4-methoxy-2H-pyran

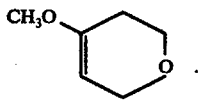

See C. B. Reese et al., J. Am. Chem. Soc. 89, 3366 (1967). The reaction condition for such vinyl ethers and unsaturates are similar to those for dihydropyran above.

In step (b) the triol acid of formula-XIV is formed by hydrolysis, opening the lactone ring. The hydrolysis occurs in a solvent containing water, for example, in methanol, dioxane, or tetrahydrofuran, in the presence of a base, such as an alkali metal hydroxide or carbonate, preferably sodium hydroxide. The reaction occurs in the range of about 0° to 100° C. and is conveniently done at ambient conditions. In this, as in all steps described herein, the duration of the reaction is determined most readily by following it with TLC. During this step the blocking groups $R_2$ are not removed.

In step (c) silylated compound XV is obtained from XIV by procedures known in the art or described herein. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include chlorotrimethylsilane, chlorotriisobutylsilane, tert-butyldimethylchlorosilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silylating agents include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

Although a wide variety of silylating agents are available, it is preferred that the silyl groups on the ring contain at least one hindered group: for example isopropyl, secondary butyl, tert-butyl, cyclohexyl, or phenyl. The silyl groups with hindered substituents are characterized as being less susceptible to hydrolysis than, for example, trimethylsilyl, and therefore resistent to replacement during subsequent steps, particularly step (e). Examples of preferred silyl groups for the cyclopentane ring are:
isopropyldimethylsilyl,
sec-butyldimethylsilyl,
tert-butyldimethylsilyl,
triisopropylsilyl,
cyclohexyldimethylsilyl,
and triphenylsilyl.

In addition to the silylation methods discussed above, it is advantageous to silylate with a chlorosilane in the presence of imidazole in a solvent such as dimethylformamide. See Corey et al., J. Am. Chem. Soc. 94, 6190 (1972). The temperature range for the reaction is about −10° to +80° C.

In step (d) the formula-XVI compound is obtained by selective hydrolysis of silyl from the terminal carboxyl group. Generally an alkali metal carbonate is employed in water and a cosolvent such as methanol, tetrahydrofuran or dioxane, in a temperature range of about −10° to +100° C. If the silyl group on the ring is hindered, a stronger base such as sodium hydroxide may be used to selectively remove the silyl group from the carboxyl.

In step (e), oxidative decarboxylation is employed to yield the formula-XVII compound. See J. D. Bacha and J. K. Kochi, Tetrahedron, 24, 2215 (1968). Compound XVI is treated in solution, for example in benzene, toluene, xylene, or heptane, with a copper (II) salt such as the acetate, chloride, or nitrate, solubilized with a compound such as pyridine, followed by a lead (IV) salt such as the acetate or benzoate. Decarboxylation may be done either thermally (60°–100° C.) or photochemically using radiation of about 3000–3700 Å as from mercury vapor lamps, in a temperature range of about 0° to 60° C.

In step (f), the compound of formula X is obtained by selective hydrolysis of the silyl groups without removing the $R_2$ blocking groups. For this purpose a base is used in a liquid medium such as dioxane or tetrahydrofuran. For unhindered silyl groups an alkali metal carbonate is useful; for hindered groups, such as tert-butyldimethylsilyl, a tetra-n-alkylammonium fluoride such as tetra-n-butylammonium fluoride is preferred, in a temperature range of −10° to +50° C.

In step (g) the formula-XI ketone is obtained by oxidation. Useful for this purpose is pyridinium chlorochromate, Collins reagent, and especially Jones reagent at about −40° C to about 25° C.

In step (h) compound XVIII is obtained by conjugative addition with a lithium diaryl cuprate reactant prepared from

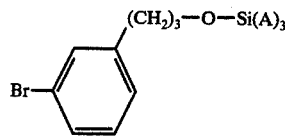

wherein $Si(A)_3$ is as defined above. For the synthesis of a cuprate reagent see, for example, Posner, Org. React. 19, 1 (1972) and Normant, Synthesis 63 (1972). See also Posner for typical conditions for addition to an enone. It is conveniently done in a solvent such as diethyl ether or tetrahydrofuran at about −78° to 0° C. A related addition has been reported by Stork et al., J. Am. Chem. Soc. 97, 4745 (1975); a non-aromatic cuprate reactant was used.

In step (i) compound XIX is obtained by reduction of the ketone, using methods known in the art, for example with sodium borohydride at about 0° C. or lithium tri(-sec-butyl)borohydride. Both $9\alpha$ and $9\beta$ hydroxy epimers may be formed in the reduction but it is not necessary to separate them for step (k).

In step (j) the terminal silyl group is removed to form compound XX, using methods described above, for example hydrolysis with tetra-n-butylammonium fluoride for tert-butyldimethylsilyl groups.

In step (k) compound XXI is obtained by oxidation, using for example the Jones reagent.

Finally, in step (1) of Chart A the $R_2$ blocking groups are removed by mild acid hydrolysis as known in the art, yielding final acid compound XL.

Chart B shows an alternate route of synthesis of the formula-X methylene compound starting with the formula-XIII lactone of Chart A. In Chart B the terms $Q_1$, $R_2$ and $R_{13}$ have the same meaning as in Chart A; $R_8$ represents (1) carboxyacyl including, for example, formula, acetyl, pivaloyl, and the like, or (2) an aromatic acyl group such as benzoyl or substituted benzoyl, non-esterified phthaloyl, naphthoyl, or substituted naphthoyl. Carboxyacyl is represented by the formula

wherein $R_9$ is hydrogen, alkyl of one to 19 carbon atoms, inclusive, or aralkyl of 7 to 12 carbon atoms, inclusive, wherein alkyl or aralkyl are substituted with zero to 3 halo atoms. Aromatic acyl groups include benzoyl and substituted benzoyl as represented by

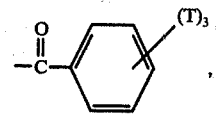

wherein T is alkyl of one to 4 carbon atoms, inclusive, phenylalkyl of 7 to 10 carbon atoms, inclusive, or nitro, and $s$ is zero to 5, inclusive, provided that not more than two T's are other than alkyl, and that the total number of carbon atoms in the T's does not exceed 10 carbon atoms; mono-esterified phthaloyl as represented by

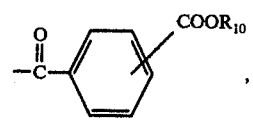

wherein $R_{10}$ is alkyl of one to 4 carbon atoms, inclusive; or naphthoyl and substituted naphthoyl as represented by

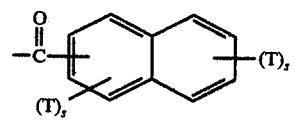

wherein T and $s$ are as defined above.

In step (a) reduction of the formula-XIII lactone yields the formula-XXII diol. For this reduction, lithium aluminum hydride or diisobutylaluminum hydride are useful at 0°– 35° C. Especially preferred is sodium bis(2-methoxyethoxy)aluminum hydride.

In step (b) the formula-XXIII diacylated compound is formed by acylation using methods known in the art or described herein. The two $R_8$ groups may be the same or different, for example one may be acetyl and the other pivaloyl. For the purpose herein it is preferred that the acyl group on the ring be somewhat more resistant to replacement by hydrolysis than the acyl group at the terminal position on the chain and one such preferred combination is with pivaloyl on the ring and acetyl on the chain. Acylation may be achieved with an acid anhydride such as acetic anhydride or with an acyl halide such as pivaloyl chloride. The reaction is done in the presence of a tertiary amine such as pyridine, triethylamine, and the like, and is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess.

Various carboxyacylating agents useful for this transformation are known in the art or readily obtainable by methods known in the art, and include carboxyacyl halides, preferably chlorides, bromides, or fluorides, i.e. $R_9C(O)Cl$, $R_9C(O)Br$, or $R_9C(O)F$, and carboxyacid anhydrides,

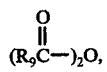

wherein $R_9$ is as defined above. Examples of acid anhydrides useful for this purpose are acetic anhydride, propionic anhydride, butyric anhydride, pentanoic anhydride, nonanoic anhydride, tridecanoic anhydride, stearic anhydride, (mono, di. or tri) chloroacetic anhydride, 3-chlorovaleric anhydride, 3-(2-bromoethyl)-4,8-dimethylnonanoic anhydride, cyclopropaneactic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, and phenoxyacetic anhydride. The choice of anhydride depends upon the identity of $R_9$ in the final acylated product, for example when $R_9$ is to be methyl, acetic anhydride is used; when $R_9$ is to be 2-chlorobutyl, 3-chlorovaleric anhydride is used.

When $R_9$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp 4 and 407 (1967) and references cited therein. Alternatively, the formula XXII diol is reacted with two equivalents of sodium hydride and then with excess ethyl formate.

In formula XXIII, $R_8$ may also represent benzoyl, substituted benzoyl, mono-esterified phthaloyl, naphthoyl or substituted naphthoyl. For introducing those blocking groups, methods known in the art are used. Thus, an aromatic acid, for example benzoic acid, is reacted with the formula-XXII compound in the presence of dehydrating agent, e.g. sulfuric acid, zinc chloride, or phosphoryl chloride; or an anhydride of the aromatic acid, for example benzoic anhydride, is used.

As examples of reagents providing $R_8$ for the purposes of this invention, the following are available as acids, anhydrides, or acyl chlorides:
benzoyl;
substituted benzoyl, e.g.
(2-, 3-, or 4-)methylbenzoyl,
(2-, 3-, or 4-(ethylbenzoyl,
(2-, 3-, or 4-)isopropylbenzyl,
(2-, 3-, or 4-)tert-butylbenzoyl,
2,4-dimethylbenzoyl,
3,5-dimethylbenzoyl,
2-isopropyltoluyl,
2,4,6-trimethylbenzoyl,
pentamethylbenzoyl,
α-phenyl-(2-, 3-, or 4-(toluyl, 2-, 3-, or 4-4-phenethylbenzoyl,
2-, 3-, or 4-nitrobenzoyl,
(2,4-, 2,5-, or 3,5-)dinitrobenzoyl,
4,5-dimethyl-2-nitrobenzoyl,
2-nitro-6-phenethylbenzoyl,
3-nitro-2-phenethylbenzoyl;
mono-esterified phthaloyl, e.g.

isophthaloyl, e.g.

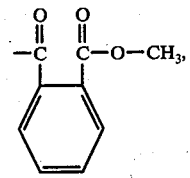

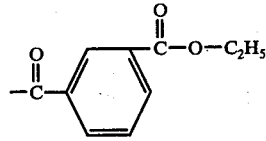

or terephthaloyl, e.g.

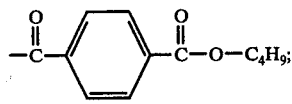

(1- or 2-)naphthoyl;
and substituted naphthoyl, e.g.
(2- 3-, 4-, 5-, 6-, or 7-)-methyl-1-naphthoyl,
(2- or 4-)ethyl-1-napthoyl,
2-isopropyl-1-naphthoyl,
4,5-dimethyl-1-naphthoyl,
6-isopropyl-4-methyl-1-naphthoyl,
8-benzyl-1-naphthoyl,
8-benzyl-1-naphthoyl,
(3-, 4-, 5-, or 8-)-nitro-1-naphthoyl,
4,5-dinitro-1-naphthoyl,
(3-, 4-, 6-, 7-, or 8)-methyl-1-naphthoyl,
4-ethyl-2-naphthoyl, and
(5- or 8 -)-nitro-2-naphthoyl.

Continuing with Chart B, in step (c) the monoacylated compound of formula XXIV is obtained by selective hydrolysis. Generally a mild base such as potassium carbonate in methanol is sufficient to deacylate the terminal group on the chain. The hydrolysis of such esters is well known in the art and a wide choice of reagents and conditions is available to one skilled in the art.

In step (d) the formula-XXV acid is formed by oxidation, employing for example, the Jones reagent (J. Chem. Soc. 39, (1946)) at $-40°$ to 25° C. in acetone.

In step (e) the formula-XXVI compound is obtained by oxidative decarboxylation, as described for Chart A above, using for example lead tetraacetate.

Finally in step (f) of Chart B the formula-X methylene compound is obtained on base hydrolysis of the monoacylated compound XXVI. Where $R_8$ is a hindered ester, stronger bases or more rigorous treatment are used than for step (c), for example with potassium carbonate at 50°–100° C. or with sodium or potassium hydroxide.

In Chart C, steps proceeding from methylene cyclopentanone derivative XI to phenylene-oxa products of formulas XLI and XLII are shown. In Chart C the terms A, Q, $Q_1$, $R_2$, $R_8$ and $R_{12}$ have the same meanings as for Charts A and B above; $R_{11}$ includes hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive.

In step (a), enone compound XI is subjected to conjugative addition with a lithium diaryl cuprate reactant prepared from

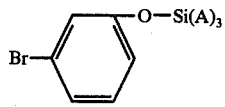

to yield compound XXVII. The term —Si(A)$_3$ is as defined above. The conditions for the reaction are similar to those described for Chart A above.

In step (b), compound XXVIII is obtained by reduction of the ketone, using methods known in the art or disclosed herein.

In step (c), the formula-XxIX acylated compound is formed by acylation of XXVIII, using methods known in the art or described herein.

In step (d) the terminal silyl group is removed to form compound XXX, using methods described above, for example hydrolysis with tetra-n-butylammonium fluoride.

In step (e) a Williamson synthesis is employed to obtain compound XXXI. The formula-XXX phenol is condensed with a haloacetate with the scope of Hal-1—CH$_2$—COOR$_{11}$ wherein Hal is chloro, bromo or iodo, and R$_{11}$ is as defined above for Chart C. Normally the reaction is done in the presence of a base such as n-butyllithium, phenyllithium, triphenylmethyllithium, sodium hydride, potassium hydride, potassium t-butoxide, sodium hydroxide, or potassium hydroxide.

In step (f) the formula-XXXII acid is obtained by base hydrolysis to replace R$_8$ and R$_{11}$ with hydrogen as is known in the art. Aqueous potassium hydroxide is useful at about 25°-100° C.

In step (g) ketone XXXIII is obtained by oxidation, using for example the Jones reagent.

In step (h) PGE-type product XLI is obtained by removing the R$_2$ blocking groups by mild acid hydrolysis as known in the art or described herein.

PGF-type products of formula XLII are obtained from intermediate XXXI by way of steps (i) and (j) of Chart C. In step (i) the R$_2$ blocking groups are removed, for example by the methods of step (h) to form compound XXXIV which is then converted to step (j) by base hydrolysis to compound XLII. The desired 9α compound is separated, if necessary, from the 9β epimer by methods known in the art, including silica gel chromatography.

Chart D shows a method for preparing inter-m-phenylene-PGF$_{1\alpha}$ compounds by way of this invention. The formula-XIX starting materials have been described above as produced by step (i) of Chart A. In Chart D, the terms A, Q$_1$, R$_2$, R$_8$, and R$_{13}$ are as defined for Chart C above.

In step (a) the formula-XIX compound is acylated at the free hydroxyl at C-9, using methods described herein or known in the art.

In step (b) the formula-XXXVI compound is obtained by preferential hydrolysis to remove the silyl groups. Thereafter, in step (c) the terminal C-1 hydroxyl groups are oxidized to carboxyl groups using methods described above for step (k) of Chart A or methods known in the art.

In step (d) the C-9 acyl blocking groups R$_8$ are removed, as by base hydrolyses following the methods described above for step (f) of Chart C. Finally in step (e) the C-11 and C-15 blocking groups R$_2$ are removed by mild acid hydrolysis as known in the art, to yield the formula-XXXIX products.

The novel intermediates of Charts A, B, C and D, including those compounds represented by formulas IX-XI and XIV-XXXVIII are frequently not isolated but used directly

CHART D

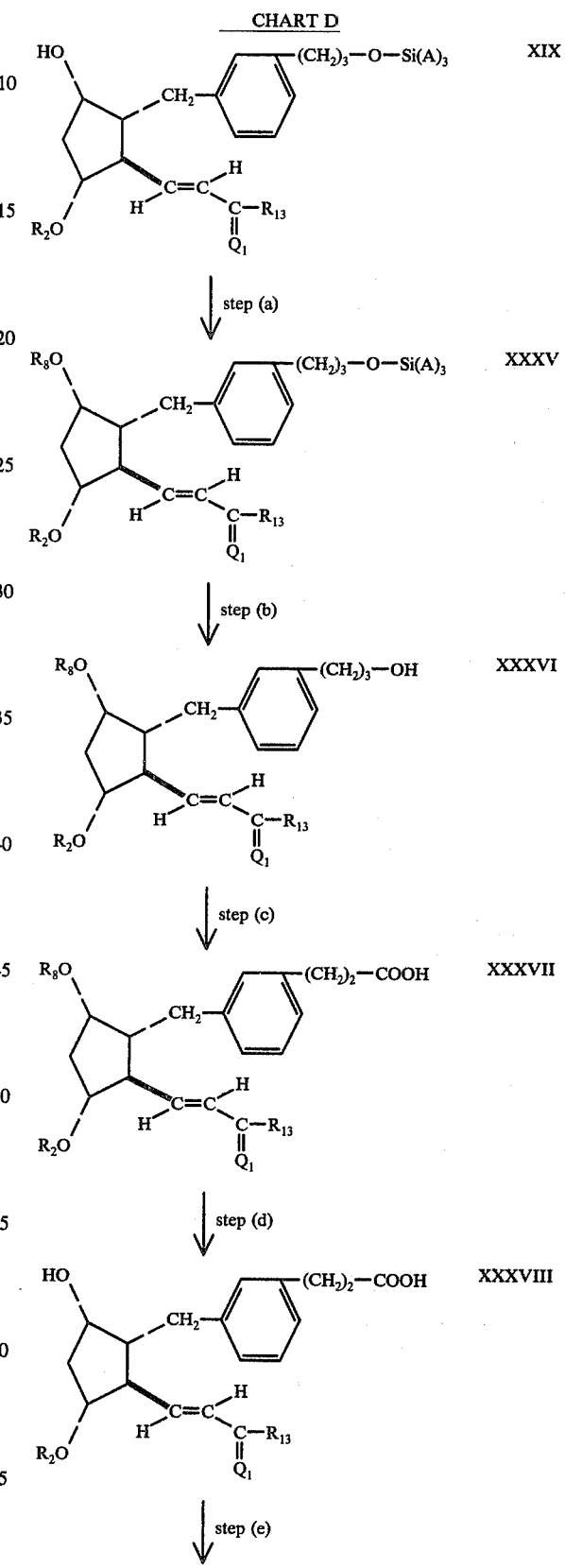

-continued
CHART D

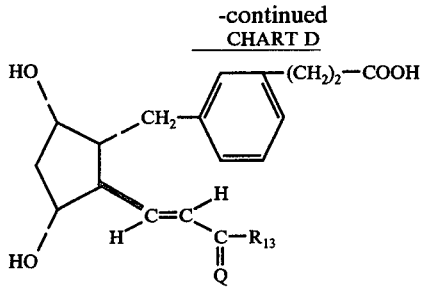

for a subsequent process step. When they are isolated, they are purified by methods known in the art, for example partition extraction, fractional crystalization, and, preferably, silica gel column chromatography.

The products represented by formulas XL, XLI, XLII, or XXXIX obtained from these intermediates retain the same stero configuration at C-15 as present in their respective starting materials of formula XII, XIII, XI, or XIX.

When an optically active intermediate or starting material is employed, subsequent steps yield optically active intermediates or products. When the racemic form of the intermediate or starting material is employed, the subsequent intermediates or products are obtained in their racemic form.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 or a Perkin-Elmer infarcord infrared spectrophotometer. Except when specified otherwise, undiluted (neat) samples are used.

NMR spectra are recorded on a Varian A-60, A-60D, or T-60 spectrophotometer using deuterochloroform solutions with tetramethylsilane as an internal standard (downfield).

Mass spectra are recorded on a CEC Model 110B Double Focusing High Resolution Mass Spectrometer or an LKB Model 9000 Gass Chromatography-Mass Spectrometer (ionization voltage 70 ev.).

Circular dichroism curves are recorded on a Cary 60 recording spectropolarimeter.

Specific rotations are determined for solutions of a compound in the specified solvent with a Perkin-Elmer Model 141 Automatic Polarimeter.

"Brine", herein, refers to an aqueous saturated sodium chloride solution.

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities.

The "A-IX system" for TLC is described by Hamberg and Samuelsson, J. Biol. Chem. 241, 257 (1966), and is based on ethyl acetate-acetic acid-2,2,4-trimethylpentanewater (90:20:50:100).

Preparation 1
3-[3(tert-butyldimethylsiloxy)propyl]-phenyllithium Cuprate Reactant 1. There is first prepared 1-bromo-3-[3-(tert-butyldimethylsilyloxy)-propyl]benzene:

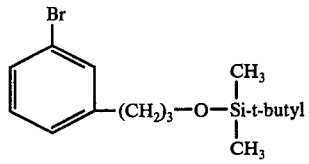

A solution of 3-(3-bromophenyl)-propan-1-ol (4.30 g.) in 15 ml. of dimethylformamide is treated with t-butyldimethylchlorosilane (3.62 g) and imidazole (3.40 g.) at 25° C. for 3.5 hr. The mixture is diluted with brine and extracted with diethyl ether-Skellysolve B (1:1). The extracts are washed with 1 N. hydrochloric acid, aqueous sodium bicarbonate and brine, and dried over magnesium sulfate. Upon concentrating, 6 g. of oil is recovered, which, on distillation yields 5.68 g. of the silyl derivative, b. 84°–86° C./0.15 mm.

II. A solution of the above bromo compound (0.82 g.) in 20 ml. of diethyl ether is treated at −78° C. with tert-butyllithium (2.25 ml. of 1.20 M. solution in pentane), and stirred for 0.5 hr. The resulting solution of aryllithium compound is added to CuI.(n-C₄H₉)₃P complex prepared independently from copper (I) iodide (0.238 g.) and tri(n-butyl)phosphine (0.253 g.) in 20 ml. diethyl ether at 25° C. for 45 min. and cooled to −78° C. The resulting lithium cuprate reagent is then used directly in solution without isolation.

EXAMPLE 1

5α-(tert-Butyldimethylsilyloxy)-3α-hydroxy-2β-[(3′S)3′-hydroxy-trans-1′-octenyl]-1α-cyclopentaneacetic Acid, 3,3′-Bistetrahydropyranyl Ether (Formula XVI: O₁ is

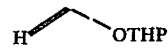

where THP is tetrahydropyran-2-yl, R₂ is THP, and Si(A)₃ is tert-butyldimethylsilyl).

I. Refer to Chart A, step (b). A solution of formula-XIII lactone, specifically 3α,5α-dihydroxy-2β-[(3′S)-3′-hydroxy-trans-1′-octenyl]-1α-cyclopentan acetic acid, bis-tetrahydropyranyl ether (Corey et al., J. Am. Chem. Soc. 92, 397 (1970), 1.14 g.) in 10 ml. of methanol is treated with 10 ml. of 1 N. aqueous sodium hydroxide at about 25° C. for 2 hr. The reaction mixture is then concentrated to about one-half its volume, diluted with 50 ml. of water and saturated with sodium chloride. The pH is adjusted to about 5–6 with 1 M. aqueous potassium hydrogen sulfate and the mixture is extracted with ethyl acetate. The organic phase is washed with brine, dried over sodium sulfate, and concentrated to the formula-XIV compound, an oil.

II. Step (c). The resulting triol acid, bistetrahydropyranyl ether is taken up in 5 ml. of dimethylformamide and added to a solution of tert-butyldimethylchlorosilane (0.94 g.) and imidazole (0.88 g.) in 15 ml. of dimethylformamide. The mixture is stirred at 25° C. and after about 17 hr. additional reagents are added (0.47 g.

of tert-butyldimethylsilyl chloride and 0.44 g. of imidazole) and stirring continued first at 25° for one hr. and then at 40° C. for 3 hr., the reaction then being complete as shown by TLC. The reaction mixture is cooled, diluted with brine, and extracted with 400 ml. of Skellysolve B-diethyl ether (1:1). The organic phase is separated, washed with 1 N. hydrochloric acid and brine, dried over sodium sulfate, and concentrated to yield the formula-XV compound.

III. Step (d). The residue from step (c) is dissolved in 175 ml. of a mixture of methanol-tetrahydrofuran-water (100:50:25) and treated with potassium carbonate (3.0 g.) at 25° C. for one hr. The reaction mixture is concentrated, diluted with 200 ml. of brine, adjusted to pH 4–5 with 1 M. aqueous potassium hydrogen sulfate, and extracted with ethyl acetate. The organic phase is washed with brine, dried over sodium sulfate, and concentrated to an oil containing the formula-XVI title compound. The product is subjected to silica gel chromatography, eluting with ethyl acetate (10–20%)-Skellysolve B, to yield the formula-XVI title compound, an oil, 1.36 g., having $R_f$ 0.14 (TLC on silica gel in ethyl acetate-Skellysolve B (1:3)), and NMR peaks at 0.3, 0.89, 0.7–2.8, 3.2–4.47, 4.68, 5.27–5.72, and 9.63 $\delta$; and IR absorption bands at 2980, 2890, 1735, 1710, 1460, 1253, 1198, 1183, 1130, 1110, 1074, 1019, 981, 870, 838 and 776 cm$^{-1}$.

EXAMPLE 2

1-(tert-Butyldimethylsilyloxy)-2-methylene-4α-hydroxy-3β-[(3'S)-3'-hydroxy-trans-1'-octenyl]cyclopentane, 4,3'-Bistetrahydropyranyl Ether (Formula XVII: $Q_1$, $R_2$, and Si(A)$_3$ as defined in Example 1).

Refer to Chart A, step (e). A mixture of the formula-XVI silylated acid (Example 1, 2.20 g.) in 35 ml. of benzene is stirred with copper (II) acetate monohydrate (0.19 g.) and 1.16 ml. of pyridine until a homogeneous solution is produced. There is then added 5.03 g. of lead tetraacetate and the mixture stirred at about 25° C. in a dark place for 1.5 hr., with a slow stream of nitrogen passing through the mixture. With continued passage of nitrogen, the mixture is heated to 80° C. within 30 min. and kept at 80° C. for an additional 45 min. The course of the reaction is monitored with TLC. The reaction mixture is finally cooled to about 25° C., diluted with 300 ml. of brine, and extracted with ethyl acetate. The organic phase is washed with brine, dried over sodium sulfate, and concentrated to a residue containing the title compound, 2.25 g. The residue is subjected to silica gel chromatography, eluting with ethyl acetate (5–45%)-Skellysolve B, to yield the formula-XVII title compound, 0.80 g., having $R_f$ 0.64 (TLC on silica gel in ethyl acetate-Skellysolve B (1:3)); NMR peaks at 0.08, 0.92, 0.75–2.9, 2.9–4.5, 4.72, 4.93, 5.17, and 5.33–5.64 $\delta$; and IR absorption bands at 2960, 2895, 1460, 1345, 1251, 1199, 1120, 1075, 1065, 1034, 1020, 1002, 973, 900, 870, 838, 817, and 775 cm$^{-1}$.

EXAMPLE 3

2-Methylene-4α-hydroxy-3β-[(3'S)-3'-hydroxy-trans-1'-octenyl]-cyclopentanol, 4,3'-Bistetrahydropyranyl Ether (Formula X: $Q_1$ and $R_2$ as defined in Example 1).

Refer to Chart A, step (f). A solution of the formula-XVII silylated compound (Example 2, 3.40 g.) in 40 ml. of tetrahydrofuran is treated with 15 ml. of 0.6 M. tetra-n-butylammonium fluoride and the mixture is stirred at about 25° C. for one hour. The resulting mixture is diluted with 300 ml. of brine and extracted with diethyl ether. The organic phase is washed with brine, dried over magnesium sulfate, and concentrated. The residue (3.77 g.) is subjected to silica gel chromatography, eluting with ethyl acetate (10–50%)-Skellysolve B, to yield the formula-X title compound, now free of silyl groups, 1.94 g., a white solid, having $R_f$ 0.19 (TLC on silica gel in ethyl acetate-Skellysolve B (1:3)). An analytical sample, obtained on recrystallizing from Skellysolve B, has m.p. 83°–84.5° C.; NMR peaks at 0.88, 0.6–2.8, 3.0–4.5, 4.70, 5.02, and 5.20–5.62 $\delta$; and IR absorption bands at 3220, 3140, 1660, 1125, 1080, 1065, 1040, 1020, 1000, 970, and 910 cm$^{-1}$.

EXAMPLE 4

2-Methylene-4α-hydroxy-3β-[(3'S)-3'-hydroxy-trans-1'-octenyl cyclopentanone, 4,3'-Bis-tetrahydropyranyl Ether (Formula XI: $Q_4$ and $R_{37}$ as defined in Example 1).

Refer to Chart A, step (g). A solution of the formula-X allylic alcohol (Example 3, 0.41 g.) in 10 ml. of acetone is treated at −20° C. with 0.50 ml. of 2.67 M. Jones Reagent (Refer to Merck Index, Eighth Edition, page 1182 and references cited therein). The mixture is stirred at −20° to −15° C. for 30 min. and is then quenched with 0.25 ml. of isopropyl alcohol, stirring for an additional 10 min. The reaction mixture is then diluted with brine and extracted with diethyl ether. The organic phase is washed with aqueous sodium bicarbonate solution and brine, dried over sodium sulfate, and concentrated to the formula-XI title compound, 0.39 g., having IR absorption bands at 2980, 1735, 1647, 1200, 1129, 1112, 1076, 1035, 1020, and 978 cm$^{-1}$; and NMR peaks at 0.91, 0.8–3.1, 3.1–4.4, 4.68, 5.11, 5.47, 5.98 $\delta$; and having $R_f$ 0.44 (TLC on silica gel in ethyl acetate-Skellysolve B (1:3)).

EXAMPLE 5

2α-[7-(tert-Butyldimethylsilyloxy)-2,3,4-trinor-1,5-inter-m-phenylene-heptyl]-4α-hydroxy-3β-[(3'S)-3'-hydroxy-trans-1-octenyl]cyclopentanone, 4,3'-Bistetrahydropyranyl Ether (Formula XVIII: $Q_1$, $R_2$, and Si(A)$_3$ as defined in Example 1).

Refer to Chart A, step (h). A solution of the formula-XI enone compound of Example 4 (0.39 g.) in 4 ml. of diethyl ether at −78° C. is added to a solution of lithium cuprate reagent (Preparation 1) at −78° C. during 5–10 min. and thereafter stirred at −78° C. for 30 min. The reaction mixture is added, with rapid stirring, to a mixture of 50 ml. of 1 M. potassium hydrogen sulfate, 50 ml. of brine, and ice, diluted with brine, and extracted with diethyl ether. The organic extracts are washed with aqueous sodium bicarbonate and brine, dried over sodium sulfate, and concentrated to an oil, 1.50 g. The oil is subjected to silica gel chromatography, eluting with ethyl acetate (10–30%)-Skellysolve B, to yield the title compound, an oil, 0.49 g., having infrared spectral absorption bands at 2980, 2890, 1749, 1251, 1200, 1128, 1108, 1077, 1037, 1020, 974, 837, 776 cm$^{-1}$; NMR peaks at 0.004, 0.9, 0.9–3.05, 3.1–4.3, 3.62, 4.63, 5.43, and 6.68–7.37 $\delta$; $R_f$ 0.30 and 0.35 (TLC on silica gel plate in ethyl acetate-Skellysolve B (1:3)).

EXAMPLE 6

2α-[7-(tert-Butyldimethylsilyloxy)-2,3,4-trinor-1,5-inter-m-phenylene-heptyl]-4α-hydroxy-3β-[(3'S)-3'-hydroxy-trans-1-octenyl]cyclopentanol, 4,3'-Bistetrahydropyranyl Ether (Formula XIX: $Q_1$, $R_2$, and Si-(A)$_3$ as defined in Example 1).

Refer to Chart A, step (i). A solution of the formula-XVIII ketone of Example 5 (0.49 g.) in 10 ml. of methanol is treated at 0° C. with sodium borohydride (0.060 g.) in 2 ml. of water. Tetrahydrofuran (5 ml.) is added and the mixture is stirred at 0° C. for 1 hr. The mixture is concentrated, diluted with brine, and extracted with ethyl acetate. The organic phase is washed with brine, dried over sodium sulfate, and concentrated to give the formula-XIX title compound and its C-9 epimer, an oil, 0.48 g., having $R_f$ 0.29 and 0.16 (TLC on silica gel plate in ethyl acetate-Skellysolve B (1:3)).

EXAMPLE 7

2α-(7-Hydroxy-2,3,4-trinor-1,5-inter-m-phenyleneheptyl)-4α-hydroxy-3β-[(3'S)-3'-hydroxy-trans-1-octenyl]cyclopentanol, 4,3'-Bistetrahydropyranyl Ether (Formula XX: $Q_1$ and $R_2$ as defined in Example 1).

Refer to Chart A, step (j). A solution of the formula-XIX reduction product (Example 6, 0.48 g.) in 10 ml. of tetrahydrofuran is treated with tetra(n-butyl)ammonium fluoride (3 ml. of 0.5 M. solution at 25° C. for 1 hr., and then with an additional 1 ml. of tetra(n-butyl)ammonium fluoride solution for an additional hour). Brine is added and the mixture is extracted with ethyl acetate. The organic phase is washed with brine, dried over sodium sulfate, and concentrated to the formula-XX title compound and its C-9 epimer, an oil, 0.57 g., having $R_f$ 0.16 and 0.08 (TLC on silica gel plate in ethyl acetate-Skellysolve B (1:1)).

EXAMPLE 8

4,5,6-Trinor-3,7-inter-m-phenylene-PGE$_1$, 11,15-Bistetrahydropyranyl Ether. (Formula XXI: $Q_1$ and $R_2$ as defined in Example 1).

Refer to Chart A, step (k). A solution of the formula-XX compound of Example 7 (0.82 g.) in 30 ml. of acetone is treated at 20° C. with Jones reagent (2.0 ml. of 2.67 M. solution prepared from 2.1 g. chromium trioxide, 6 ml. of water and 1.7 ml. of concentrated sulfuric acid). After 1.6 hr. the reaction is complete and is quenched with 1.0 ml. of isopropyl alcohol, at 0° C. for 10 min. The mixture is diluted with brine and extracted with ethyl acetate. The organic phase is washed with brine, dried over sodium sulfate and concentrated to formula-XXI title compound, an oil, 0.86 g., having $R_f$ = 0.59 (TLC on silica gel plate in A-IX system).

EXAMPLE 9

4,5,6-Trinor-3,7-inter-m-phenylene-PGE$_1$ (Formula IV: Q is

Refer to Chart A, step (1). A solution of the formula-XXI compound of Example 8 (0.86 g.) in 15 ml. of acetic acid-water-tetrahydrofuran (20:10:3) is left at about 25° C. for 19 hr. The mixture is then diluted with 20 ml. of water and concentrated. The residue is taken up in 5 ml. of dichloromethane and subjected to silica gel chromatography, eluting with ethyl acetate (50-100%)-Skellysolve B, to yield the formula-IV title compound, 0.25 g., m 67°-77° C., $R_f$ 0.19 (TLC on silica gel in A-IX system). An analytical sample, obtained by recrystallizing from diethyl ether-Skellysolve B, has m.p. 65.9°-69.5° C.; NMR peaks at 0.95, 1.2-1.7, 1.9-3.2, 3.9-4.2, 5.3-5.7, 5.9-6.2, and 6.9-7,3 δ; [α]$_D$ −87° (c = 0.8465 in chloroform); and mass spectral peaks (TMS derivative) at 604.3408, 589, 533, 514, 499, 443, 417, 389, 313, 279, and 199.

Following the procedures of Examples -9 but replacing the formula-XIII lactone starting material with the appropriate lactone wherein the terminal pentyl group of the octenyl side chain of 3α,5α-dihydroxy-2β-[(3'S)-3'-hydroxy-trans-1'-octenyl]-1α-cyclopentanacetic acid, bis-tetrahydropyranyl ether is replaced by each of the following groups, as known in the art or available by methods known in the art:

1-methylpentyl
1,1-dimethylpentyl
1-fluoropentyl
1,1-difluoropentyl
phenoxymethyl
(m-tolyloxy)methyl
(p-tolyloxy)methyl
(m-chlorophenoxy)methyl
(p-chlorophenoxy)methyl
(m-fluorophenoxy)methyl
(p-fluorophenoxy)methyl
(m-trichloromethylphenoxy)methyl
(p-trichloromethylphenoxy)methyl
(m-anisyloxy)methyl
(p-anisyloxy)methyl
1phenoxyethyl
1-methyl-1-phenoxyethyl
benzyl
2-phenethyl
2-(m-tolyl)ethyl
2-(p-tolyl)ethyl
2-(m-chlorophenyl)ethyl
2-(p-chlorophenyl)ethyl
2-(m-fluorophenyl)ethyl
2-(p-fluorophenyl)ethyl
2-(m-trichloromethylphenyl)ethyl
2-(p-trichloromethylphenyl)ethyl
2-(m-anisyl)ethyl
2-(p-anisyl)ethyl
3-phenylpropyl
1-methyl-1-phenylethyl
1-methyl-2-phenylethyl
1,1-dimethyl-2-phenylethyl
1,1-dimethyl-3-phenylpropyl
α,α-difluorobenzyl
1-fluoro-2-phenylethyl
1,1-difluoro-2-phenylethyl and
1,1-difluoro-3-phenylpropyl there are obtained each of the corresponding formula-XL 4,5,6-trinor-3,7-inter-m-phenylene-PGE$_1$ analogs having one of the following structural features:

16-methyl-;
16,16-dimethyl-;
16-fluoro-;
16,16-difluoro-;
16-phenoxy-17,18,19,20-tetranor-;
16-(m-tolyloxy)-17,18,19,20-tetranor-;
16-(p-tolyloxy)-17,18,19,20-tetranor-;
16-(m-chlorophenoxy)-17,18,19,20-tetranor-;
16-(p-chlorophenoxy)-17,18,19,20-tetranor-;
16-(m-fluorophenoxy)-17,18,19,20-tetranor-;
16-(p-fluorophenoxy)-17,18,19,20-tetranor-;
16-(m-trichloromethylphenoxy)-17,18,19,20-tetranor-;
16-(p-trichloromethylphenoxy)-17,18,19,20-tetranor-;
16-(m-anisyloxy)-17,18,19,20-tetranor-;
16-(p-anisyloxy)-17,18,19,20-tetranor-;
16-phenoxy-18,19,20-trinor-;

16-methyl-16-phenoxy-18,19,20-trinor;
16-phenyl-17,18,19,20-tetranor-;
17-phenyl-18,19,20-trinor-;
17-(m-tolyl)-18,19,20-trinor-;
17-(p-tolyl)-18,19,20-trinor-;
17-(m-chlorophenyl)-18,19,20-trinor-;
17-(p-chlorophenyl)-18,19,20-trinor-;
17-(m-fluorophenyl)-18,19,20-trinor-;
17-(p-fluorophenyl)-18,19,20-trinor-;
17-(m-trichloromethylphenyl)-18,19,20-trinor-;
17-(p-trichloromethylphenyl)-18,19,20-trinor-;
17-(m-anisyl)-18,19,20-trinor-;
17-(p-anisyl)-18,19,20-trinor-;
18-phenyl-19,20-dinor-;
16-methyl-16-phenyl-18,19,20-trinor-;
16-methyl-17-phenyl-18,19,20-trinor-;
16,16-dimethyl-17-phenyl-18,19,20-trinor-;
16,16-dimethyl-18-phenyl-19,20-dinor-;
16,16-difluoro-16-phenyl-17,18,19,20-tetranor-;
16-fluoro-17-phenyl-18,19,20-trinor-;
16,16-difluoro-17-phenyl-18,19,20-trinor-; or
16,16-difluoro-18-phenyl-19,20-dinor-.

For example, starting with 3α,5α-dihydroxy-2β-[(3'S)-3'-hydroxy-trans-1'-(5'-phenyl)pentenyl]-1α-cyclopentanacetic acid, bis tetranhydropyranyl ether there is obtained 4,5,6,18,19,20-hexanor-3,7-inter-m-phenylene-17-phenyl-PGE$_1$.

Likewise starting with the corresponding (3'R)-3'-hydroxy lactones, there are obtained the 15-epimeric products.

EXAMPLE 10

2-methylene-4α-hydroxy-3β-[(3'S)-3'-hydroxy-trans-1'-octenyl]-cyclopentanol, 4,3'-Bistetrahydropyranyl Ether (Formula X: O$_1$ and R$_2$ as defined in Example 1).

a. Refer to Chart B, step (a). A solution of formula-XIII lactone (Corey et al., J. Am. Chem. Soc. 92, 397 (1970), 4.29 g.) in 15 ml. of tetrahydrofuran is added dropwise to a stirred mixture of sodium bis(2-methoxyethoxy)aluminum hydride (70% solution in benzene, 4.3 g.) and 50 ml. of tetrahydrofuran at about 20° C. The mixture is stirred for an additional 2 hr. whereupon 100 ml. of 5% aqueous potassium hydroxide is added cautiously with stirring. The mixture is diluted with 200 ml. of diethyl ether and water (1:1). The organic phase is washed with 5% aqueous potassium hydroxide and brine, dried over sodium sulfate, and concentrated to yield the formula-XXII compound, an oil, 4.59 g., having infrared absorption bands at 3450, 2980, 2890, 1465, 1450, 1438, 1346, 1338, 1200, 1130, 1110, 1075, 1034, 1020, 974, and 869 cm$^{-1}$.

b. Chart B, step (b). The diacylated formula-XXIII compound is next obtained from the diol product XXII of step (a) (4.59 g.) treated in 40 ml. of pyridine, and 10 ml. of acetic anhydride together with 0.1 g. of 4-dimethylaminopyridine as a catalyst. The reaction mixture is stirred at about 25° C. for 16 hr., then diluted with brine and extracted with diethyl ether. The organic phase is washed with ice-cold 1 M. potassium acid sulfate and brine, dried over sodium sulfate, and concentrated to yield the formula-XXIII diacetate, an oil, 5.24 g.

c. Chart B, step (c). The product of step (b) (5.24 g.) is treated with potassium carbonate (0.14 g.) in 100 ml. methanol at about 40° C. for 1.25 hr. and finally at about 25° C. for 0.75 hr. The mixture is diluted with ice cold brine and 1 M. potassium acid sulfate to pH 2-3 and extracted with ethyl acetate. The organic phase is washed with brine, dried over sodium sulfate, and concentrated to an oil containing the formula-XXIV monoacetate, 4.56 g. The residue is subjected to silica gel chromatography, eluting with acetone (5–75%)-dichloromethane to obtain the formula-XXIV compound, an oil, 0.69 g., having R$_f$ 0.20 (TLC on silica gel in acetonedichloromethane (15:85)); infrared absorption bands at 3530, 2970, 1740, 1242, 1130, 1111, 1073, 1032, 1020, 972 cm$^{-1}$; NMR peaks at 0.88, 0.7-3.0, 2.03, 3.15–4.3, 4.65, 5.13, 5.3-5.82 δ.

d. Chart B, step (d). The product of step (c) (0.69 g.) in 20 ml. of acetone is treated with 1.5 ml. of 2.67 M. Jones reagent added dropwise. The mixture is stirred at about 25° C. for 0.5 hr., diluted with brine, and extracted with diethyl ether. The ether extract is washed with brine, dried over sodium sulfate, and concentrated to an oil, 0.58g. The residue is subjected to silica gel chromatography, eluting with ethyl acetate (10–50%)-Skellysolve B, to obtain the formula-XXV acid compound, 0.31 g., having R$_f$ 0.56 and 0.51 (TLC on silica gel in A-IX system); infrared absorption bands at 2970, 1745, 1240, 1032, and 1020 cm$^{-1}$; and NMR peaks at 0.89, 0.7–3.1, 2.05, 3.15–4.4, 4.65, 5.19, 5.46, 9.06 δ.

e. Chart B, step (e). The product of step (d) (0.31 g.) is treated in 10 ml. of benzene with 0.12 ml. of pyridine and 0.02 g. of copper (II) acetate monohydrate. After stirring in a dark place at about 25° C. for 45 min., the mixture is treated with 0.52 g. of lead tetraacetate. The mixture is stirred, first at about 25° C. for 45 min., then heated up to 80° C. in 15 min. and at 80° C. for 10 min. The mixture is cooled, diluted with brine, and extracted with ethyl acetate. The organic phase is washed with brine, dried over sodium sulfate, and concentrated to an oil, 0.37 g. The residue is subjected to silica gel chromatography, eluting with ethyl acetate (20-50%)-Skellysolve B, to yield the formula-XXVI methylene compound, 0.03 g., having R$_f$ 0.61 (TLC on silica gel in ethyl acetate-Skellysolve B(1:1); infrared absorption bands at 2970, 1740, 1235, 1035, and 1020 cm$^{-1}$; and NMR peaks at 0.90, 0.8-3.0, 2.07, 3.1-4.3, 4.67, 5.00, 5.27, and 5.43 δ.

f. Chart B, step (f). Finally, the formula-X title compound is obtained by saponification of the remaining acyl group on the product of step (e) (0.03 g.) treated in 2 ml. of methanol with 0.02 g. of potassium carbonate at about 25° C. for 45 min. The reaction mixture is diluted with brine and extracted with ethyl acetate. The extract is washed with brine, dried over sodium sulfate, and concentrated to yield the title compound, an oil, 0.22 g., having R$_f$ identical with that for the formula-X product of Example 3 above.

EXAMPLE 11

2-Methylene-4α-hydroxy-3β-[(3'S)-3'-hydroxy-trans-1'-octenyl]-cyclopentanol, 4.3'-Bistetrahydropyranyl Ether (Formula X: Q$_1$ and R$_2$ as defined in Example 1).

a. Refer to Chart B, step (b). The compound of formula-XXIII wherein R$_8$ in the terminal position of the chain is acetyl and R$_8$ on the ring is pivaloyl is prepared in two stages. The monoacetate is first prepared from compound XXII (Example 10-a, 5.56 g.), 50 ml. of pyridine, and 1.45 ml. of acetic anhydride, stirred at 0° C. for 2 hr., then allowed to warm to about 20° C. in 16 hr. The mixture is diluted with brine and extracted with ethyl acetate. The organic phase is washed with 1 N. hydrochloric acid to pH 2 in the washings, then with brine, dried, and concentrated to an oil, 5.88 g. The residue is subjected to silica gel chromatography, elution with ethyl acetate (10–100%)-Skellysolve B, to yield the monoacetate, 3.41 g., having R$_f$ 0.29 (TLC on silica gel in ethyl acetate-Skellysolve B (1:1); infrared absorption bands at 3530, 2975, 2890, 1745, 1239, 1133, 1077, 1032, 1020 and 981 cm$^{-1}$; and NMR peaks at 0.89, 0.9–2.8, 2.04, 3.1–4.38, 4.15, 4.72 and 5.53.

b. Continuing with Chart B, step (b). The product of step (a) above, having a terminal acetyl group on the chain (3.41 g.) is treated with 30 ml. of pyridine and 1.74 ml. of pivaloyl chloride at about 25° C. for 12 hr. The reaction is continued with additional 1.74 ml. of pivaloyl chloride at 40° C for 3 hr. and at 23° C. for 16 hr. The reaction is quenched with 4 ml. of 85% lactic acid at 23° C. for 1 hr. The mixture is diluted with brine and extracted with ethyl acetate. The extract is washed with 1 N. hydrochloric acid-ice, sodium bicarbonate, and brine, dried over sodium sulfate, and concentrated to the formula-XXIII compound having acetyl on the terminal position of the chain and pivaloyl on the ring. There is obtained 3.84 g., having R$_f$0.59 (TLC on silica gel in ethyl acetate-Skellysolve B (1:1)); infrared absorption bands at 2980, 2890, 1745, 1755, 1280, 1160, 1032, and 1020 cm$^{-1}$; and NMR peaks at 0.87, 1.19, 1.98, 4.03, 4.67, 5.10, and 5.52 δ.

c. Chart B, step (c). The product of step (b) above (3.84 g.) is treated in 100 ml. of anhydrous methanol with 0.09 g. of potassium carbonate at about 25° C. for 0.5 hr. and at 40° C. for 1.5 hr. The reaction is continued with additional 0.09 g. of potassium carbonate at 40° C. for 2 hr. and at 24° C. for 16 hr. The mixture is concentrated and then diluted with brine and extracted with ethyl acetate. The organic phase is washed with brine, dried over sodium sulfate, and concentrated to yield the formula-XXIV product wherein R$_8$ is pivaloyl and R$_2$ is THP. There is obtained 3.42 g., having R$_f$0.34 (TLC on silica gel in ethyl acetate-Skellysolve B (1:1)).

d. Chart B, step (d). The product of step (c) above (3.42 g.) is oxidized to the formula-XXV acid in 75 ml. of acetone at 0° C. with 6.54 ml. of 2.67 M. Jones reagent. In one hour the reaction is quenched with 2 ml. of isopropyl alcohol, stirring at 0° C. for 15 min. The mixture is concentrated, diluted with brine, and extracted with ethyl acetate. The extract is washed with water and brine, dried over sodium sulfate, and concentrated to an oil, 3.44 g. The residue is subjected to silica gel chromatography, eluting with ethyl acetate (20–40%)-Skellysolve B to yield the formula-XXV acid, an oil, 1.99 g., having R$_f$0.69 and 0.74 (TLC on silica gel in A-IX system); and NMR peaks at 0.88, 1.18, 0.8–3.0, 3.1–4.3, 4.67, 5.16, 5.48, and 10.54 δ.

e. Chart B, step (e). The product of step (d) above is subjected to oxidative decarboxylation to form the formula-XXVI compound. The formula-XXV acid (1.99 g.) is treated in 35 ml. of benzene with 0.18 g. of copper (I) acetate monohydrate and 1.11 ml. of pyridine at about 25° C. for one hour. Lead tetraacetate (4.80 g.) is added and stirring continued in a dark place at about 25° C. for one hour, then to 80° C. in 10 min. and at 80° C. for 25 min. The mixture is cooled, and diluted with brine, and extracted with ethyl acetate. The extract is washed with brine, dried over sodium sulfate, and concentrated to an oil, 2.11 g. The residue is subjected to silica gel chromatography, eluting with ethyl acetate (5–40%)-Skellysolve B, to yield the formula-XXVI methylene compound wherein R$_8$ is pivaloyl and R$_2$ is THP. There is obtained an oil, 0.15 g., having R$_f$0.43 (TLC on silica gel in ethyl acetate-Skellysolve B (1:3)) and NMR peaks at 0.88, 0-8-2.9, 1.18, 3.0-4,4, 4.72, 5.00, 5.22, 5.45 δ f. Chart B, step (f). Finally, the formula-X title compound is obtained by saponification of the product of step (e) above, using excess sodium hydroxide in aqueous methanol at about 25° C. until shown by TLC to be converted. Thereafter the usual work-up with brine, extracting, washing, and concentrating yields the title compound having the same properties as the product of Example 3 above.

Following the procedures of Examples 1-4, 10 and 11 but replacing starting material XIII, i.e. 3α,5α-dihydroxy-2β-[(3'S)-3'-hydroxy-trans-1'-octenyl]-1α-cyclopentanacetic acid, bistetrahydropyranyl ether with each of the formula-XIII lactones listed following Example 9, there are obtained the corresponding formula-XI enone compounds having the substituted side chains.

Preparation 2

3-(tert-Butyldimethylsilyloxy)-phenylithium Cuprate Reactant

I. There is first prepared 1-bromo-3-(tert-butyldimethylsilyloxy)benzene:

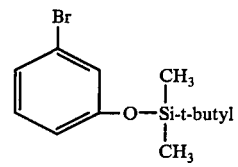

A solution of m-bromophenol (10.0 g.) in 40 ml. of dimethylformamide is treated with t-butyldimethylchlorosilane (17.42 g.) and imidazole (15.74 g.) at 23° C. for 16 hr. The mixture is diluted with brine and extracted with Skellysolve B-dichloromethane (3:1). The extracts are washed with brine, dried over sodium sulfate, and concentrated to an oil, 29.07 g. The oil is distilled to give the desired 1-bromo-3-(tert-butyldimethylsilyloxy)benzene, 13.47 g., b.p. 66° C. (0.28 mm.).

II. A solution of the above bromo compound (4.40 g.) in 75 ml. of diethyl ether is treated at −78° C. with tertbutyllithium (12.14 ml. of 1.26 M. solution in pentane) and stirred for 40 min. The resulting solution of aryllithium compound is added to CuI.tri-n-butylphosphine complex prepared independently from copper (I) iodide (1.55 g.) and tri(n-butyl)phosphine (1.55 g.) in 50 ml. of diethyl ether at 25° C. for 45 min. The resulting lithium cuprate reagent is used directly without isolation.

EXAMPLE 12

2α-[m-(tert-Butyldimethylsilyloxy)benzyl]-4α-hydroxy-3β-[(3'S)-3'-hydroxy-trans-1-octenyl]cyclopentanone, 4,3'-Bistetrahydropyranyl Ether (Formula XXVII: Q$_1$, R$_2$, and Si(A)$_3$ as defined in Example 1).

Refer to Chart C, step (a). A solution of the formula-XI enone compound of Example 4 (2.49 g.) in 30 ml. of diethyl ether at −78° C. is added to a solution of lithium cuprate reagent (Preparation 2) at −78° C. during 15 min. with vigorous stirring and thereafter stirred for 30 min. The reaction mixture is added, with vigorous stirring to a mixture of 25 ml. of acetate acid in 225 ml. of diethyl ether at −78° C. The resulting solution is warmed to about 25° C., washed with brine and aqueous sodium bicarbonate and concentrated to an oil, 8.9 g. The oil is subjected to silica gel chromatography, eluting with ethyl acetate (10–40%)-Skellysolve B to yield the formula-XXVII title compound, an oil, 3.36 g., having NMR peaks 4.4, 0.18, 0.90, 0.98, 0.6–3.1, 3.2–4,4, 4.68, 5.50, and 6.52-7.42 δ; infrared absorption bands at 2970, 2890, 1750, 1612, 1583, 1485, 1470, 1440, 1272, 1258, 1200, 1160, 1132, 1129, 1112, 1080, 1037, 1020, 976, and 784 cm$^{-1}$; and R$_f$ 0.29 and 0.34 (TLC on silica gel in ethyl acetate-Skellysolve B (1:3)).

EXAMPLE 13

2α-[3-(tert-Butyldimethylsilyloxy)benzyl]-4α-hydroxy-3β-[(3'S)-3'-hydroxy-trans-1-octenyl]cyclopentanol, 4,3'-Bistetrahydropyranyl Ether (Formula XXVIII: Q$_1$, R$_2$, and Si(A)$_3$ as defined in Example 1).

Refer to Chart C, step (b). A solution of the formula-XXVII ketone (Example 12, 3.2 g.) in 30 ml. of tetrahydrofuran is added dropwise to a mixture of lithium tri-(secbutylborohydride) (8.2 ml. of 1 M. solution in tetrahydrofuran) in 50 ml. of tetrahydrofuran at −78° C. and the mixture is stirred at −78° C. for 2 hr. The reaction mixture is quenched with 5 ml. of water and 2 ml. of 30% hydrogen peroxide and warmed to about 25° C. in 1 hr. The mixture is diluted with 500 ml. of brine and extracted with ethyl acetate. The extracts are washed with brine, dried over magnesium sulfate, and concentrated to yield the formula-XXVIII title compound, an oil, 3.54 g., having R$_f$ 0.30 (TLC on silica gel in ethyl acetate-Skellysolve B (1:3)).

EXAMPLE 14

3α-Hydroxy-5α-acetoxy-2β-[(3'S)-3'-hydroxy-trans-1-octenyl]-1α-[3-(tert-butyldimethylsilyloxy)benzyl]-cyclopentane, 3,4'-Bis-tetrahydropyranyl Ether (Formula XXIX: R$_8$ is acetyl, and Q$_1$, R$_2$, and Si(A)$_3$ are as defined in Example 1).

Refer to Chart C, step (c). A solution of the formula-XXVIII hydroxy compound (Example 13, 3.54 g.) in 30 ml. of pyridine is treated at 0° C. with 7 ml. of acetic anhydride and 0.32 g. of 4-dimethylaminopyridine and stirred at 0° C. for one hr., finally at about 25° C. for 1.75 hr. The mixture is diluted with 400 ml. of brine, and extracted with ethyl acetate. The extracts are washed with brine, ice-cold 1 N. aqueous hydrochloric acid, saturated aqueous sodium bicarbonate, and brine, dried over sodium sulfate, and concentrated to the formula-XXIX title compound, an oil, 3.49 g., having R$_f$ 0.44 (TLC on silica gel in ethyl acetate-Skellysolve B (1:3)).

EXAMPLE 15

3α-Hydroxy-5α-acetoxy-2β-[(3's)-3'-hydroxy-trans-1-octenyl-1α-(m-hydroxybenzyl)-cyclopentane, 3,3'-Bistetrahydropyranyl Ether (Formula XXX: Q$_1$, R$_2$, and R$_8$ are as defined in Example 14).

Refer to Chart C, step (d). A solution of the formula-XXIX silyl derivative (Example 14, 3.49 g.) in 15 ml. of tetrahydrofuran is treated with 14.4 ml. of 0.5 M. tetra-n-butylammonium fluoride in tetrahydrofran at about 25° C. for 1.5 hr. The mixture is diluted with 200 ml. of brine and extracted with ethyl acetate. The extracts are washed with saturated aqueous sodium bicarbonate and brine, dried over sodium sulfate, and concentrated to an oil, 3.71 g. The oil is subjected to silica gel chromatography, eluting with ethyl acetate (25–55%)-Skellysolve B to yield the formula-XXX title compound, an oil, 2.25 g., having R$_f$ 0.11 (TLC on silica gel in ethyl acetate-Skellysolve B (1:3)); NMR peaks at 0.88, 2.06, 0.7–3.0, 3.10–4.37, 4.48–5.04, 5.56, 6.37-7.38, and 7.06 δ; and infrared absorption bands at 3390, 2960, 2885, 1737, 1715, 1590, 1446, 1368, 1237, 1100, 1152, 1128, 1073, 1020, and 972 cm$^{-1}$.

EXAMPLE 16

3-Oxa-4,5,6-trinor-3,7-inter-m-phenylene-PGF$_{1α}$, 9-Acetate, 11,15-Bistetrahydropyranyl Ether, Methyl Ester (Formula XXXI: R$_{11}$ is methyl, and Q$_1$, R$_2$, and R$_8$ are as defined in Example 14).

Refer to Chart C, step (e). A mixture of the formula-XXX phenol (Example 15, 2.48 g.) in 30 ml. of 1,2-dimethoxyethane, methyl bromoacetate (1.39 g.) and 0.29 g. of 57% sodium hydride dispersion is stirred at about 25° C. for 2 hr. The mixture is then treated with 2 ml. of glacial acetic acid, diluted with brine, and extracted with ethyl acetate. The extract is washed with saturated aqueous sodium bicarbonate and brine, dried over magnesium sulfate, and concentrated to the formula-XXXI title compound, an oil, 3.20 g., having R$_f$ 0.48 in acetone-dichloromethane (15:85).

EXAMPLE 17

3-Oxa-4,5,6-trinor-3,7-inter-m-phenylene-PGF$_{1α}$, 11,15-Bistetrahydropyranyl Ether (Formula XXXII: Q$_1$ and R$_2$ as defined in Example 1).

Refer to Chart C, step (f). A mixture of the formula-XXXI diester (Example 16, 2.45 g.) in 100 ml. of methanol and 30 ml. of 5% aqueous potassium hydroxide is heated at reflux for 5 hr., cooled, diluted with brine-ice, acidified to pH 3 with 1 M. aqueous potassium hydrogen sulfate, and extracted with ethyl acetate. The extracts are washed with brine, dried over sodium sulfate, and concentrated to formula-XXXII title compound, 2.46 g.

EXAMPLE 18

3-Oxa-4,5,6-trinor-3,7-inter-m-phenylene-PGE$_1$, 11,15-Bistetrahydropyranyl Ether (Formula XXXIII: Q$_1$ and R$_2$ as defined in Example 1) and 3-Oxa-4,5,6-trinor-3,7-inter-m-phenylene-PGE$_1$ (Formula VI: Q is

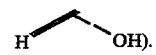

I Refer to Chart C, step (g). A solution of the formula-XXXII PGF$_{1α}$-type compound (Example 18, 2.46 g.) in 100 ml. of acetone is cooled to −20° C. and treated with 1.76 ml. of 2.67 M. Jones Reagent, stirring at −20° to −15° C. for 45 min. The reaction mixture is quenched with 3 ml. of isopropyl alcohol, stirred 10 min. more, diluted with brine, and extracted with ethyl acetate. The extracts are washed with brine, dried over sodium sulfate, and concentrated to the formula-XXXIII title compound, 2.17 g.

II. Step (h). A solution of the above bistetrahydropyranyl ether (2.17 g.) in 5 ml. of tetrahydrofuran, 30 ml. of acetic acid, and 15 ml. of water is stirred at 40° C. for 2.5 hr. The reaction mixture is then diluted with 300 ml. of water and freeze-dried to a semisolid residue containing the formula-VI title compound. The residue is subjected to silica gel chromatography, eluting with ethyl acetate (50–100%)-hexane to yield the formula-VI title compound, 0.77 g. Recrystallization from ethyl acetate-hexane gave colorless crystals, m.p. 134.5°–136.5° C.

EXAMPLE 19

3-Oxa-4,5,6-trinor-3,7-inter-m-phenylene-PGF$_{1\alpha}$, 9-Acetate, Methyl Ester (Formula XXXIV: Q is

R$_8$ is acetyl, and R$_{11}$ is methyl); and 3-Oxa-4,5,6-trinor-3,7-inter-m-phenylene-PGF$_{1\alpha}$ (Formula VII: Q is

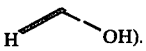

1. Refer to Chart C, step (i). A mixture of the formula-XXXI compound (Example 16, 0.75 g.) in 2 ml. of tetrahydrofuran, 10 ml. of acetic acid, and 5 ml. of water is stirred at 35° C. for 1.5 hr. and at 25° C. for 2 hr. The mixture is diluted with brine and extracted with ethyl acetate. The extract is washed with saturated aqueous sodium bicarbonate and brine, dried over sodium sulfate, and concentrated to the formula-XXXIV diester, an oil, 0.60 g.

II. Step (j). A solution of the above diester (0.60 g.) in 10 ml. of methanol is treated with 5 ml. of 5% aqueous potassium hydroxide at 25° C. for 12 hr. and then at reflux for 2 hr. The mixture is cooled, diluted with ice-cold brine, acidified to pH 3 with 1 M. aqueous potassium hydrogen sulfate, and extracted with ethyl acetate. The extracts are washed with brine, dried over sodium sulfate, and concentrated to a residue, 0.44 g. The residue is subjected to silica gel chromatography, eluting with acetone (20–100%)-dichloromethane to yield the formula-VII title compound, 0.23 g., a solid. The product is recrystallized from ethyl acetate-hexane to yield colorless crystals, m.p. 100.1°–108.3° C., R$_f$0.06 (TLC on silica gel in A-IX system); NMR peaks at 0.88, 0.6–3.2, 3.97, 4.58, 4.64, 5.53, and 6.52–7.50 δ; infrared absorption bands at 3460, 3300, 2740, 2610, 2550, 1720, 1605, 1595, 1495, 1275, 1235, 1195, 1080, 1055, 1025, 975, 945 cm$^{-1}$; [α]$_D$-18° (C. 0.7145 in ethanol); and mass spectral ions at 665.3512, 680, 609, 590, 575, 549, 519, 500, 443, 404, 353, 314, 237, and 217.

Following the procedures of Examples 12–19 but replacing the starting material XI, i.e. 2-methylene-4α-hydroxy-3β-[(3'S)-3'-hydroxy-trans-1'-octenyl]cyclopentanone, with each of the formula-XI enones following Example 11, there are obtained each of the corresponding 3-oxa-4,5,6-trinor-3,7-inter-m-phenylene-PGF$_{1\alpha}$-analogs having the structural features for the PGE$_1$ analogs obtained following Example 9.

EXAMPLE 20

2-Decarboxy-2-hydroxymethyl-4,5,6-trinor-3,7-inter-m-phenylene-PGF$_{1\alpha}$, 9-Acetate (Formula XXXVI: Q$_1$ is

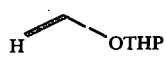

where THP is tetrahydropyranyl, R$_8$ is acetyl, R$_2$ is THP, and R$_{13}$ is n-pentyl).

Refer to Chart D, steps (a) and (b). A solution of compound XIX (Example 6, 1.26 g.) in 15 ml. of pyridine is treated with 5 ml. of acetic anhydride and warmed to 45°–50° C. for 20 hr. The reaction mixture is diluted with brine and extracted with ethyl acetate. The combined extracts are washed with water, 1N hydrochloric acid, saturated aqueous sodium bicarbonate, and brine, dried over sodium sulfate and concentrated to yield the formula-XXXV compound, an oil, having R$_f$ 0.37 (TLC on silica gel in 25% ethyl acetate in Skellysolve B).

A solution of the above formula-XXXV compound in 18 ml. of tetrahydrofuran is treated with 7 ml. of 0.5 M tetra-n-butylammonium fluoride in tetrahydrofuran. The reaction mixture is stirred at about 25° C. for 2.25 hr., diluted with brine and extracted with ethyl acetate. The combined extracts are washed with brine, dried over sodium sulfate, and concentrated. The residue is subjected to silica gel chromatography, eluting with ethyl acetate (30–60%)-Skellysolve B, to yield the title compound of formula XXXVI, 0.823 g., having R$_f$0.42 (TLC on silica gel in A-IX system.

EXAMPLE 21

4,5,6-trinor-3,7-inter-m-phenylene-PGF$_{1\alpha}$ (Formula XXXIX: Q is

and R$_{13}$ is n-pentyl).

Refer to Chart D steps (c), (d), and (e). A solution of alcohol XXXVI (Example 20, 0.84 g.) in 30 ml. of acetone is treated at −20° C. with 1 ml. of 2.67 M Jones Reagent. After one hr. the reaction is quenched with 0.5 ml. of isopropanol. The reaction mixture is diluted with brine and extracted with ethyl acetate. The combined extracts are washed with brine, dried over sodium sulfate, and concentrated to yield the formula-XXXVII acid, 0.89 g., having R$_f$0.58 (TLC on silica gel in A-IX system).

A solution of above acid XXXVII (0.89 g.) in 15 ml. of methanol is treated with 5 ml. of 5% aqueous potassium hydroxide and heated at reflux for 40 min. The reaction mixture is cooled to about 25° C., diluted with brine, acidified to pH 2–3 with ice-cold 1 M aqueous potassium hydrogen sulfate, and extracted with ethyl acetate. The combined extracts are washed with brine, dried over sodium sulfate, and concentrated to yield the formula-XXXVIII compound, 0.78 g., an oil having R$_f$ 0.42 (TLC on silica gel in A-IX system).

A solution of the above formula-XXXVIII compound (0.78 g.) in 15 ml. of acetic acid/water/tetrahydrofuran (20/10/3 by volume) is stirred at about 25° C. for 18 hr. The reaction mixture is then freeze-dried. The residue is subjected to silica gel chromatography, eluting with ethyl acetate (50–100%)-Skellysolve B followed by methanol (5%) in ethyl acetate, to give the formula XXXIX (V) title compound, 0.27 g., a solid having R$_f$0.12 (TLC on silica gel in A-IX system). An analytical sample, obtained by recrystallizing from ethyl acetate-Skellysolve B, has m.p. 109.8°–112.0° C; NMR peaks at 0.88, 3.67–4.23, 5.02, 5.43–5.67, and 6.8–7.3 δ; and mass spectral peaks at 372, 354, 300, 191, 163, 121, 117, 93, 91, 79, 67, 43, and 41.

Following the procedures of Examples 20 and 21 but replacing starting material XIX, i.e. 2α-[7-(tert-Butyldimethylsilyloxy)-2,3,4-trinor-1,5-inter-m-phenyleneheptyl]-4α-hydroxy-3β-[(3'S)-3'-hydroxy-trans-1-octenyl]cyclopentanol, 4,3'-bistetrahydropyranyl ether with each of the formula-XIX intermediates obtained from the formula-XIII lactones listed following Example 9, there are obtained each of the corresponding formula-XXXIX 4,5,6-trinor-3,7-inter-m-phenylene-PGF$_{1\alpha}$ analog having the structural features listed for the PGE$_1$ analogs obtained following Example 9.

I claim:

1. A prostaglandin analog of the formula

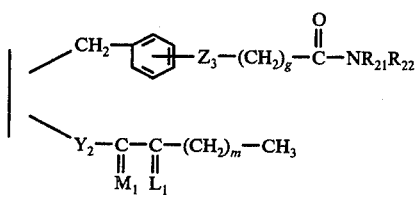

wherein D is

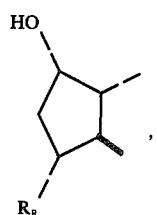,

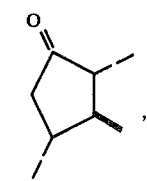,

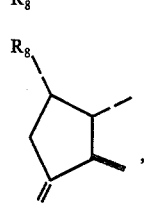,

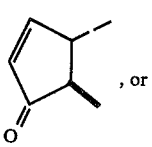, or

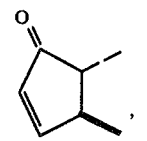, wherein R$_8$ is hydrogen or hydroxy;
wherein Y$_2$ is
(1) trans—CH=CH—, or
(2) cis—CH=CH—,
wherein g is one, 2, or 3;
wherein Z$_3$ is oxa or methylene;
wherein L$_1$ is

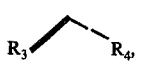

or a mixture of

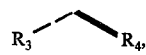

and

, wherein R$_3$ and R$_4$ are hydrogen, methyl, or fluoro, being the same or different, with the proviso that one of R$_3$ and R$_4$ is methyl only when the other is hydrogen or methyl;
wherein M$_1$ is

or

, wherein R$_5$ is hydrogen or methyl;
wherein m is one to 5, inclusive; and
wherein R$_{21}$ and R$_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy or nitro;
(vii) hydroxyalkyl of one to 4 carbon atoms, inclusive;
(viii) dihydroxyalkyl of one to 4 carbon atoms; or
(ix) trihydroxyalkyl of one to 4 carbon atoms;
with the further proviso that not more than one of R$_{21}$ and R$_{22}$ is other than hydrogen or alkyl.

2. A prostaglandin analog according to claim 1, wherein D is

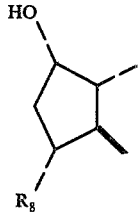

3. A prostaglandin analog according to claim 2, wherein R$_8$ is hydrogen.

4. 3,7-inter-m-Phenylene-3-oxa-4,5,6-trinor-11-deoxy-PGF$_{1\alpha}$, amide, a prostaglandin analog according to claim 3.

5. A prostaglandin analog according to claim 2, wherein R$_8$ is hydroxy.

6. 3,7-inter-m-Phenylene-3-oxa-4,5,6-trinor-PGF$_{1\alpha}$, amide, a prostaglandin analog according to claim 5.

7. A prostaglandin analog according to claim 1, wherein D is

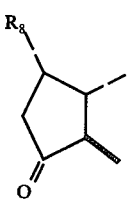

8. A prostaglandin analog according to claim 7, wherein $R_8$ is hydrogen.

9. 3,7-inter-m-Phenylene-3-oxa-4,5,6-trinor-9-deoxy-PGD$_1$, amide, a prostaglandin analog according to claim 8.

10. A prostaglandin analog according to claim 7, wherein $R_8$ is hydrogen.

11. 3,7-inter-m-Phenylene-3-oxa-4,5,6-trinor-PGD$_1$, amide, a prostaglandin analog according to claim 10.

12. A prostaglandin analog according to claim 1, wherein D is

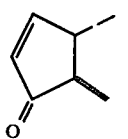

13. 3,7-inter-m-Phenylene-3-oxa-4,5,6-trinor-9-deoxy-9,10-didehydro-PGD$_1$, amide, a prostaglandin analog according to claim 12.

14. A prostaglandin analog according to claim 1, wherein D is

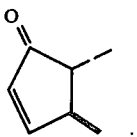

15. 3,7-inter-m-Phenylene-3-oxa-4,5,6-trinor-PGA$_1$, amide, a prostaglandin analog according to claim 14.

16. A prostaglandin analog according to claim 1, wherein D is

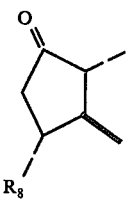

17. A prostaglandin analog according to claim 16, wherein $R_8$ is hydrogen.

18. 3,7-inter-m-Phenylene-3-oxa-4,5,6-trinor-13,14-dihydro-11-deoxy-PGE$_1$, amide, a prostaglandin analog according to claim 17.

19. A prostaglandin analog according to claim 16, wherein $R_8$ is hydroxy.

20. A prostaglandin analog according to claim 19, wherein $Y_2$ is cis—CH═CH—.

21. 3,7-inter-m-Phenylene-3-oxa-4,5,6-trinor-cis-13-PGE$_1$, amide, a prostaglandin analog according to claim 20.

22. A prostaglandin analog according to claim 19, wherein $Y_2$ is trans—CH═CH—.

23. A prostaglandin analog according to claim 22, wherein $Z_3$ is methylene.

24. A prostaglandin analog according to claim 23, wherein $Z_3$ is attached to the phenyl ring in the position meta to methylene.

25. 3,7-inter-m-Phenylene-4,5,6-trinor-PGE$_1$, amide, a prostaglandin analog according to claim 24.

26. A prostaglandin analog according to claim 22, wherein $Z_3$ is oxa.

27. A prostaglandin analog according to claim 26, wherein $M_1$ is

28. 15-epi-3,7-inter-m-Phenylene-3-oxa-4,5,6-trinor-PGE$_1$, amide, a prostaglandin analog according to claim 27.

29. A prostaglandin analog according to claim 26, wherein $M_1$ is

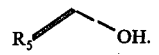

30. A prostaglandin analog according to claim 29, wherein $Z_3$ is attached to the phenyl ring in the position meta to methylene.

31. A prostaglandin analog according to claim 30, wherein $m$ is 3.

32. A prostaglandin analog according to claim 31, wherein $g$ is 3.

33. 2a,2b-Dihomo-3,7-inter-m-phenylene-3-oxa-4,5,6-trinor-PGE$_1$, amide, a prostaglandin analog according to claim 32.

34. A prostaglandin analog according to claim 31, wherein $g$ is one.

35. A prostaglandin analog according to claim 34, wherein at least one of $R_3$ and $R_4$ is methyl.

36. 3,7-inter-m-Phenylene-3-oxa-4,5,6-trinor-16,16-dimethyl-PGE$_1$, amide, a prostaglandin analog according to claim 35.

37. A prostaglandin analog according to claim 34, wherein at least one of $R_3$ and $R_4$ is fluoro.

38. 3,7-inter-m-Phenylene-3-oxa-4,5,6-trinor-16,16-difluoro-PGE$_1$, amide, a prostaglandin according to claim 37.

39. A prostaglandin analog according to claim 34, wherein $R_3$ and $R_4$ are both hydrogen.

40. A prostaglandin analog according to claim 39, wherein $R_5$ is methyl.

41. 3,7-inter-m-Phenylene-3-oxa-4,5,6-trinor-15-methyl-PGE$_1$, amide, a prostaglandin analog according to claim 40.

42. A prostaglandin analog according to claim 37, wherein $R_5$ is hydrogen.

43. 3,7-inter-m-Phenylene-3-oxa-4,5,6-trinor-PGE$_1$, n-propylamide, a prostaglandin analog according to claim 42.

44. 3,7-inter-m-Phenylene-3-oxa-4,5,6-trinor-PGE$_1$, ethylamide, a prostaglandin analog according to claim 42.

45. 3,7-inter-m-Phenylene-3-oxa-4,5,6-trinor-PGE$_1$, methylamide, a prostaglandin analog according to claim 42.

46. 3,7-inter-m-Phenylene-3-oxa-4,5,6-trinor-PGE$_1$, amide, a prostaglandin analog according to claim 42.

* * * * *

UNITED STATES PATENT OFFICE
CERTIFICATE OF CORRECTION

Patent No. 4,100,192     Dated 11 July 1978

Inventor(s) W. Morozowich

It is certified that error appears in the above-identified patent and that said Letters Patent are hereby corrected as shown below:

Column 45, line 35, "$O_1$ and $R_2$" should read -- $Q_1$ and $R_2$ --;
Column 49, line 3, "NMR peaks 4.4, 0.18," should read -- NMR peaks at 0.18, --; line 50, "-2β-[(3's)-3'-hydroxy-" should read -- -2β-[(3'S)-3'-hydroxy- --;
Column 53, line 9-15, should read as follows:

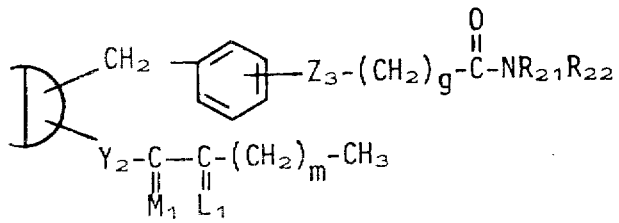

Column 55, lines 59-60, "4,5,6-trinor-13,14-dihydro-11-deoxy-$PGE_1$," should read -- 4,5,6-trinor-11-deoxy-$PGE_1$, --.

Signed and Sealed this

Eighth Day of September 1981

[SEAL]

Attest:

Attesting Officer

GERALD J. MOSSINGHOFF
Commissioner of Patents and Trademarks

UNITED STATES PATENT OFFICE
CERTIFICATE OF CORRECTION

Patent No. 4,100,192  Dated 11 July 1978

Inventor(s) W. Morozowich

It is certified that error appears in the above-identified patent and that said Letters Patent are hereby corrected as shown below:

Column 7, line 22, "4-chloro-4-chloro-3-" should read -- 4-chloro-3- --;
Column 9, line 56, "mose especially 1," should read -- most especially 1, --; line 1, "4-methyl-62-pyridylbutylamide" should read -- 4-methyl-β-pyridylbutylamide --
Column 10, line 4, "to product" should read -- to produce --;
Column 12, lines 19-20, "plateletto glass" should read -- platelet-to-glass --;
Column 14, line 11, ", is an 11-deoxy-PGE-type" should read -- , D is an 11-deoxy-PGE-type --;
Column 15, lines 24-25, "4,5,6,18,19,20-trinor-" should read -- 4,5,6,18,19,20-hexanor- --;
Column 18, line 32, "Afer six min." should read -- After six min. --;
Column 23, line 41, "1-(2-nahthyl-" should read -- 1-(2-napthyl- --;
Column 24, line 7, "-$CH_2$-$CH_2$-$CH_2$-$CH_2$-$CF_2$," should read -- -$CH_2$-$CH_2$-$CH_2$-$CH_2$-$CH_2$-$CF_2$, --;
Column 28, lines 57-65, that portion of Formula XXXVI reading

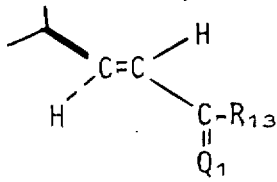   should read   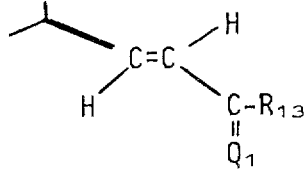

Column 31, lines 2-10, that portion of Formula XXXIV reading

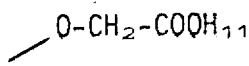   should read   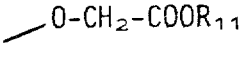

Column 33, lines 59-60, "formula, acetyl," should read -- formyl, acetyl, --;
Column 35, line 61, "α-phenyl-(2-, 3-, or 4-(toluyl, 2-, 3-, or 4-4-phenethylbenzoyl," should read -- α-phenyl-(2-, 3-, or 4-)toluyl, 2-, 3-, or 4-phenethylbenzoyl, --;
Column 40, line 41, "$O_1$ is" should read -- $Q_1$ is --;